(12) United States Patent
Plos et al.

(10) Patent No.: US 7,204,860 B2
(45) Date of Patent: Apr. 17, 2007

(54) COMPOSITION FOR DYEING HUMAN KERATIN MATERIALS, COMPRISING AT LEAST ONE FLUORESCENT DYE AND AT LEAST ONE POLYOL, PROCESS THEREFOR AND USE THEREOF

(75) Inventors: Grégory Plos, Paris (FR); Luc Gourlaouen, Asnieres (FR)

(73) Assignee: L'Oreal, Paris (FR)

( * ) Notice: Subject to any disclaimer, the term of this patent is extended or adjusted under 35 U.S.C. 154(b) by 295 days.

(21) Appl. No.: 10/814,300

(22) Filed: Apr. 1, 2004

(65) Prior Publication Data

US 2005/0008594 A1 Jan. 13, 2005

Related U.S. Application Data

(60) Provisional application No. 60/468,086, filed on May 6, 2003.

(30) Foreign Application Priority Data

Apr. 1, 2003 (FR) .................................. 03 04030

(51) Int. Cl.
*A61K 7/13* (2006.01)
(52) U.S. Cl. ........................ 8/405; 8/406; 8/407; 8/410; 8/411; 8/421; 8/611; 8/648; 132/202; 132/208
(58) Field of Classification Search .................... 8/405, 8/406, 407, 410, 411, 421, 611, 648; 132/202, 132/208
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Ditmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. |
| 3,658,985 A | 4/1972 | Olson, Jr. et al. |
| 3,856,550 A | 12/1974 | Bens et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,237,243 A | 12/1980 | Quack et al. |
| 4,240,450 A | 12/1980 | Grollier et al. |
| 4,256,458 A | 3/1981 | Degen et al. |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |

(Continued)

FOREIGN PATENT DOCUMENTS

AT 302 534 10/1972

(Continued)

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.

(Continued)

*Primary Examiner*—Eisa Elhilo
(74) *Attorney, Agent, or Firm*—Finnegan Henderson Farabow Garrett & Dunner, L.L.P.

(57) ABSTRACT

Disclosed herein are compositions comprising at least one fluorescent dye and at least one polyol, processes using this composition and a device therefor. Further disclosed herein is the use of a composition for dyeing a human keratin material, such as artificially dyed or pigmented hair and dark skin, with a lightening effect, comprising at least one fluorescent dye and at least one polyol.

54 Claims, No Drawings

U.S. PATENT DOCUMENTS

| | | | |
|---|---|---|---|
| 4,517,174 A | 5/1985 | Jacquet et al. | |
| 4,591,610 A | 5/1986 | Grollier | |
| 4,608,250 A | 8/1986 | Jacquet et al. | |
| 4,693,935 A | 9/1987 | Mazurek | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,781,724 A | 11/1988 | Wajaroff et al. | |
| 4,823,985 A | 4/1989 | Grollier et al. | |
| 4,839,166 A | 6/1989 | Grollier et al. | |
| 4,948,579 A | 8/1990 | Jacquet et al. | |
| 4,961,925 A | 10/1990 | Tsujino et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,057,311 A | 10/1991 | Hanazawa et al. | |
| 5,089,252 A | 2/1992 | Grollier et al. | |
| 5,139,037 A | 8/1992 | Grollier et al. | |
| 5,188,639 A | 2/1993 | Schultz et al. | |
| 5,196,189 A | 3/1993 | Jacquet et al. | |
| 5,275,808 A | 1/1994 | De Groot et al. | |
| 5,316,551 A | 5/1994 | Wenke | |
| 5,356,438 A | 10/1994 | Kim et al. | |
| 5,445,655 A | 8/1995 | Kuhn et al. | |
| 5,635,461 A | 6/1997 | Onitsuka et al. | |
| 5,708,151 A | 1/1998 | Mockli | |
| 5,733,343 A | 3/1998 | Mockli | |
| 5,744,127 A * | 4/1998 | Giuseppe et al. | 424/59 |
| 5,792,221 A | 8/1998 | Lagrange et al. | |
| 5,830,446 A | 11/1998 | Berthiaume et al. | |
| 5,833,997 A | 11/1998 | Mahieu et al. | |
| 5,853,708 A | 12/1998 | Cauwet et al. | |
| 5,873,494 A | 2/1999 | Dallas, Jr. | |
| 5,958,392 A | 9/1999 | Grollier et al. | |
| 5,961,667 A | 10/1999 | Doehling et al. | |
| 5,962,522 A | 10/1999 | Wacher et al. | |
| 6,001,135 A | 12/1999 | Rondeau et al. | |
| 6,106,577 A | 8/2000 | Audousset et al. | |
| 6,120,780 A | 9/2000 | Dupuis et al. | |
| 6,156,077 A | 12/2000 | Shibata et al. | |
| 6,180,666 B1 | 1/2001 | Wacher et al. | |
| 6,260,556 B1 | 7/2001 | Legrand et al. | |
| 6,375,958 B1 | 4/2002 | Cauwet et al. | |
| 6,391,062 B1 * | 5/2002 | Vandenbossche et al. | 8/405 |
| 6,436,151 B2 | 8/2002 | Cottard et al. | |
| 6,436,153 B2 * | 8/2002 | Rondeau | 8/426 |
| 6,475,248 B2 | 11/2002 | Ohashi et al. | |
| 6,570,019 B2 | 5/2003 | Pasquier et al. | |
| 6,576,024 B1 | 6/2003 | Lang et al. | |
| 6,592,630 B2 | 7/2003 | Matsunaga et al. | |
| 6,616,709 B2 | 9/2003 | Ohashi et al. | |
| 6,712,861 B2 | 3/2004 | Rondeau | |
| 2001/0010812 A1 | 8/2001 | Chevalier et al. | |
| 2001/0023514 A1 | 9/2001 | Cottard et al. | |
| 2001/0023515 A1 | 9/2001 | Cottard et al. | |
| 2001/0031270 A1 | 10/2001 | Douin et al. | |
| 2001/0034914 A1 | 11/2001 | Saunier et al. | |
| 2001/0054206 A1* | 12/2001 | Matsunaga et al. | 8/405 |
| 2001/0055580 A1 | 12/2001 | Belli et al. | |
| 2002/0004956 A1 | 1/2002 | Rondeau | |
| 2002/0012681 A1 | 1/2002 | George et al. | |
| 2002/0026676 A1 | 3/2002 | Ohashi et al. | |
| 2002/0034489 A1 | 3/2002 | Wiegland et al. | |
| 2002/0046431 A1 | 4/2002 | Laurent et al. | |
| 2002/0046432 A1 | 4/2002 | Rondeau | |
| 2002/0088063 A1 | 7/2002 | Ohashi et al. | |
| 2002/0131941 A1 | 9/2002 | Habeck et al. | |
| 2002/0176836 A9 | 11/2002 | Belli et al. | |
| 2002/0176875 A9 | 11/2002 | Douin et al. | |
| 2003/0000023 A9 | 1/2003 | Rondeau | |
| 2003/0019052 A1* | 1/2003 | Pratt | 8/405 |
| 2003/0019053 A9 | 1/2003 | Rondeau | |
| 2003/0055268 A1 | 3/2003 | Pasquier et al. | |
| 2003/0074747 A1 | 4/2003 | Vuarier et al. | |
| 2003/0124079 A1 | 7/2003 | Mougin et al. | |
| 2003/0131424 A1 | 7/2003 | Audousset et al. | |
| 2004/0019981 A1 | 2/2004 | Cottard et al. | |
| 2004/0034945 A1 | 2/2004 | Javet et al. | |
| 2004/0037796 A1 | 2/2004 | Cottard et al. | |
| 2004/0049860 A1 | 3/2004 | Cottard et al. | |
| 2004/0105830 A1 | 6/2004 | Boswell et al. | |
| 2004/0141943 A1 | 7/2004 | Mougin et al. | |
| 2004/0148711 A1 | 8/2004 | Rondeau | |
| 2004/0205901 A1 | 10/2004 | Cottard et al. | |
| 2004/0258641 A1 | 12/2004 | Plos et al. | |
| 2005/0005368 A1 | 1/2005 | Plos et al. | |
| 2005/0005369 A1 | 1/2005 | Plos et al. | |
| 2005/0008593 A1 | 1/2005 | Plos et al. | |
| 2005/0028301 A1 | 2/2005 | Pastore | |
| 2005/0144741 A1 | 7/2005 | Lang et al. | |

FOREIGN PATENT DOCUMENTS

| | | |
|---|---|---|
| CA | 1255603 | 6/1989 |
| CH | 487 231 | 3/1970 |
| DE | 33 133 32 | 10/1994 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 815 828 B1 | 6/1999 |
| EP | 0 970 684 A1 | 1/2000 |
| EP | 1 023 891 B1 | 8/2000 |
| EP | 1142559 A2 * | 4/2001 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |
| FR | 2393573 | 1/1979 |

| | | |
|---|---|---|
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2 773 470 | 7/1999 |
| FR | 2 797 877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-236929 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 99/36045 | 7/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

Co-pending U.S. Appl. No. 10/814,333, filed Apr. 1, 2004.
Co-pending U.S. Appl. No. 10/814,334, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,335, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Apr. 1, 2004.
Co-pending U.S. Appl. No. 10/814,336, filed Apr. 1, 2004.
English Language Derwent Abstract of DE 33 133 32.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2 773 470.
English Language Derwent Abstract of FR 2,797,877.
English Language Derwent Abstract of 2,800,612.
English Language Abstract of FR 2 589 476 (EP 0 225 261) from EPO website.
English Language Derwent Abstract of JP 10-236929.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Abstract of JP 2001-294519 from Japio database.
English Language JPO Abstract Abstract of JP 2002-47151.
English Language Derwent Abstract of JP 2001-516701.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Derwent Abstract of JP 2004-59468.
English Language Derwent Abstract of JP 2-200612.
English Language Derwent Abstract of JP 6-183935.
English Language Derwent Abstract of JP 6-227954.
English Language Derwent Abstract of JP 8-183716.

English Language Derwent Abstract of JP 8-208448.
English Language Derwent Abstract of WO 02/32386.
French Search Report for French Patent Application No. FR 02/16669, priority document for co-pending U.S. Appl. No. 10/742,995, Aug. 6, 2003.
French Search Report for French Patent Application No. FR 03/04021, priority document for U.S. Appl. No. 10/814,337, Dec. 8, 2003.
French Search Report for French Patent Application No. FR 03/04022, priority document for co-pending U.S. Appl. No. 10/814,336, Nov. 20, 2003.
French Search Report for French Patent Application No. FR 03/04024, priority document for co-pending U.S. Appl. No. 10/814,585, Dec. 8, 2003.
French Search Report for French Patent Application No. FR 03/04026, priority document for co-pending U.S. Appl. No. 10/814,335, Nov. 21, 2003.
French Search Report for French Patent Application No. FR 03/04027, priority document for co-pending U.S. Appl. No. 10/814,428, Nov. 28, 2003.
French Search Report for French Patent Application No. FR 03/04028, priority document for co-pending U.S. Appl. No. 10/814,236, Nov. 25, 2003.
French Search Report for French Patent Application No. FR 03/04029, priority document for co-pending U.S. Appl. No. 10/814,430, Feb. 5, 2004.
French Search Report for French Patent Application No. FR 03/04030, priority document for co-pending U.S. Appl. No. 10/814,300, Nov. 27, 2003.
French Search Report for French Patent Application No. FR 03/04031, priority document for co-pending U.S. Appl. No. 10/814,333, Jan. 8, 2004.
French Search Report for French Patent Application No. FR 03/04033, priority document for co-pending U.S. Appl. No. 10/814,334, Nov. 28, 2003.
French Search Report for French Patent Application No. FR 03/04034, priority document for co-pending U.S. Appl. No. 10/814,338, Feb. 17, 2004.
French Search Report for French Patent Application No. FR 03/04035, priority document for co-pending U.S. Appl. No. 10/814,305, Feb. 5, 2004.
International Search Report for PCT Application No. PCT/FR 02/03252, (for co-pending U.S. Appl. No. 10/490,869, Jan. 20, 2003.
Office Action mailed Nov. 17, 2005 in co-pending U.S. Appl. No. 10/814,336.
Office Action mailed Nov. 3, 2005 in co-pending U.S. Appl. No. 10/490,869.
Office Action mailed May 26, 2006 in co-pending U.S. Appl. No. 10/490,869.
Office Action mailed Nov. 2, 2005 in co-pending U.S. Appl. No. 10/814,338.
Office Action mailed May 30, 2006 in co-pending U.S. Appl. No. 10/814,338.
Office Action mailed Nov. 2, 2005 in co-pending U.S. Appl. No. 10/742,995.
Office Action mailed May 18, 2006 in co-pending U.S. Appl. No. 10/814,333.
Office Action mailed Mar. 27, 2006 in co-pending U.S. Appl. No. 10/814,334.
Office Action mailed Mar. 15, 2006 in co-pending U.S. Appl. No. 10/814,305.
Office Action mailed May 25, 2006 in co-pending U.S. Appl. No. 10/814,335.
Office Action mailed Mar. 24, 2006 in co-pending U.S. Appl. No. 10/814,236.
Office Action mailed Mar. 15, 2006 in co-pending U.S. Appl. No. 10/814,337.
Jacobi, Otto and Jacobi, Gertrud, "Investigation into the reciprocal action of cosmetics and the biosphere of the stratum corneum of the skin," *Cosmetics and Toiletries*, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
D.F. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci. 271:380-389 (1993).
Zviak, C., The Science of Hair Care, pp. 215 and 278 (1986).
English language Derwent Abstract of JP 2001-302473.
English language Derwent Abstract of JP 2002-326911.
English language Derwent Abstract of JP 9-183714.
Mishra, J.K. et al. "Synthesis of some bischromophoric dyes containing nonabsorbing flexible bridge," Indian Journal of Chemistry, vol. 31B, pp. 118-122, Feb. 1992.
Office Action mailed Apr. 6, 2006, in co-pending U.S. Appl. No. 10/742,995.
Office Action mailed Aug. 24, 2006, in co-pending U.S. Appl. No. 10/814,305.
Office Action mailed Aug. 28, 2006, in co-pending U.S. Appl. No. 10/814,236.
Office Action mailed Jul. 7, 2006, in co-pending U.S. Appl. No. 10/814,585.
Office Action mailed Jun. 21, 2006, in co-pending U.S. Appl. No. 10/814,336.
Office Action mailed Jun. 8, 2006, in co-pending U.S. Appl. No. 10/814,430.
Office Action mailed Mar. 15, 2006, in co-pending U.S. Appl. No. 10/814,305.
Office Action mailed Oct. 23, 2006, in co-pending U.S. Appl. No. 10/742,995.

* cited by examiner

COMPOSITION FOR DYEING HUMAN KERATIN MATERIALS, COMPRISING AT LEAST ONE FLUORESCENT DYE AND AT LEAST ONE POLYOL, PROCESS THEREFOR AND USE THEREOF

This application claims benefit of U.S. Provisional Application No. 60/468,086, filed May 6, 2003.

Disclosed herein are compositions comprising at least one fluorescent dye and at least one polyol, and processes and a device for using this composition. Further disclosed herein is the use of a composition comprising at least one fluorescent dye and at least one polyol to dye with a lightening effect human keratin materials, for example, keratin fibers such as artificially dyed or pigmented hair, and dark skin.

It is common for individuals with dark skin to wish to lighten their skin and for this purpose to use cosmetic or dermatological compositions containing bleaching agents.

The substances most commonly used as bleaching agents are hydroquinone and its derivatives, kojic acid and its derivatives, azelaic acid, and arbutin and its derivatives, alone or in combination with other active agents.

However, these agents have some drawbacks. For example, they need to be used for a long time and in large amounts in order to obtain a bleaching effect on the skin. No immediate effect is observed upon applying compositions comprising them.

In addition, hydroquinone and its derivatives are used in amounts that are effective to produce a visible bleaching effect. For example, hydroquinone is known for its cytotoxicity towards melanocyte.

Moreover, kojic acid and its derivatives have the drawback of being expensive and consequently of not being able to be used in large amounts in products for commercial mass distribution.

There is thus still a need for cosmetic compositions that can allow a lighter, uniform, homogeneous skin tone of natural appearance to be obtained, and at the same time, can have satisfactory transparency after application to the skin.

In the field of haircare, there are two major types of hair dyeing.

The first type is semi-permanent dyeing or direct dyeing, which uses dyes capable of giving the hair's natural color a more or less pronounced modification that can withstand shampooing several times. These dyes are known as direct dyes and may be used in two different ways. The colorations may be performed by applying a composition comprising at least one direct dye directly to the keratin fibers, or by applying a mixture, prepared extemporaneously, of a composition comprising at least one direct dye with a composition comprising at least one oxidizing bleaching agent, which is, for example, aqueous hydrogen peroxide solution. Such a process is then termed "lightening direct dyeing."

The second type is permanent dyeing or oxidation dyeing. This can be performed with "oxidation" dye precursors, which are colorless or weakly colored compounds which, once mixed with oxidizing products, at the time of use, can give rise to colored compounds and dyes via a process of oxidative condensation. At least one direct dye is often used in combination with the oxidation bases and couplers in order to neutralize or attenuate the shades with too much of a red, orange or golden glint, or to the contrary, to accentuate these red, orange or golden glints.

Among the available direct dyes, nitrobenzene direct dyes may not be sufficiently strong, and indoamines, quinone dyes and natural dyes may have low affinity for keratin fibers and consequently lead to colorations that are not sufficiently fast with respect to the various treatments to which the keratin fibers may be subjected, such as shampooing.

In addition, there is a need to obtain a lightening effect on human keratin fibers. This lightening has conventionally been obtained via a process of bleaching the melanins of the hair via an oxidizing system generally comprising hydrogen peroxide optionally combined with persalts. This bleaching system may have the drawback of degrading the keratin fibers and of impairing their cosmetic properties.

Therefore, there is still a need to solve at least one of the problems mentioned above, and, for example, to provide a composition that can have good dyeing affinity for keratin materials such as keratin fibers, good resistance properties with respect to external agents, such as with respect to shampooing, and that can also make it possible to obtain lightening without impairing the treated material, such as the keratin fibers.

It has thus been found, surprisingly and unexpectedly, that the use of fluorescent dyes, such as those in the orange range, in the presence of particular polyols, can satisfy at least one of these needs.

Disclosed herein is thus a composition comprising, in a cosmetically acceptable medium, at least one fluorescent dye that is soluble in the medium and at least one polyol with a molecular weight of less than 500 g/mol and comprising more than three carbon atoms, of formula (I) below:

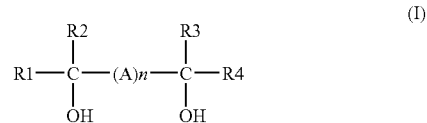

wherein:

A is a divalent radical of a hydrocarbon-based chain chosen from linear and branched, saturated and unsaturated hydrocarbon-based chains, optionally interrupted with from 2 to 10 hetero atoms and comprising from 1 to 35 carbon atoms, $R_1$, $R_2$, $R_3$ and $R_4$, which may be identical or different, are each chosen from a hydrogen atom, $C_1$–$C_2$ alkyl radicals, and $C_1$–$C_6$ mono- and polyhydroxyalkyl radicals, and n is 0 or 1;

provided that the composition does not comprise, as a fluorescent agent, 2-[2-(4-dialkylamino)phenylethenyl]-1-alkylpyridinium wherein the alkyl radical of the pyridinium nucleus is a methyl or ethyl radical, the alkyl radical of the benzene nucleus is a methyl radical, and the counterion is a halide.

Further disclosed herein is a process for dyeing keratin fibers, such as human keratin fibers, with a lightening effect, comprising:
a) applying to the keratin fibers a composition disclosed herein for a time that is sufficient to develop a desired coloration and lightening,
b) optionally rinsing the keratin fibers,
c) optionally washing the keratin fibers with shampoo and rinsing the keratin fibers, and
d) drying the keratin fibers or leaving the keratin fibers to dry.

Further disclosed herein is a process for coloring dark skin with a lightening effect, comprising applying to the skin a composition disclosed herein and drying the skin or leaving the skin to dry.

Also disclosed herein is the use of a composition for dyeing human keratin materials with a lightening effect, wherein the composition comprises, in a cosmetically acceptable medium, at least one fluorescent dye that is soluble in the medium, and at least one polyol with a molecular weight of less than 500 g/mol and comprising more than three carbon atoms, of formula (I) below:

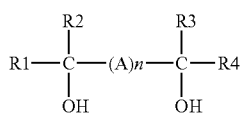

wherein:

A is a divalent radical of a hydrocarbon-based chain chosen from linear and branched, saturated and unsaturated hydrocarbon-based chains, optionally interrupted with from 2 to 10 hetero atoms and comprising from 1 to 35 carbon atoms, $R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and n is 0 or 1.

The composition disclosed herein can, for example, allow better fixing of the fluorescent dye onto the keratin materials, which is reflected by an increased fluorescent effect and a lightening effect that is greater than that obtained with the fluorescent dye used alone.

Better resistance of the result with respect to washing or shampooing can also be obtained.

However, other characteristics and advantages of the present disclosure will emerge more clearly on reading the description and the examples that follow.

Unless otherwise indicated, the limits of the ranges of values that are given in the description are included in these ranges.

Thus, as has been mentioned previously, the composition disclosed herein comprises, in a cosmetically acceptable medium, at least one fluorescent dye that is soluble in the medium and at least one polyol with a molecular weight of less than 500 g/mol and comprising more than three carbon atoms, of formula (I) below:

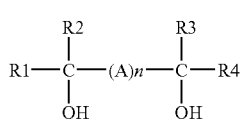

wherein:

A is a divalent radical of a hydrocarbon chain chosen from linear and branched, saturated and unsaturated hydrocarbon-based chains, optionally interrupted with from 2 to 10 hetero atoms chosen, for example, from oxygen and nitrogen atoms, and comprising from 1 to 35 carbon atoms, $R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and n is 0 or 1.

In one embodiment, the hydrocarbon-based chain of the divalent radical A in the formula (I) does not comprise any hetero atoms.

For example, the radical A is chosen from linear and branched alkylene groups comprising from 1 to 8 carbon atoms.

As polyols of the formula (I) that may be used herein, mention may be made, for example, of 1,4-butanediol, 1,5-pentanediol, 1,6-hexanediol, neopentyl glycol (2,2-dimethyl-1,3-propanediol), isoprene glycol (3-methyl-1,3-butanediol), 2,3-dimethyl-1,5-pentanediol, 2-methyl-1,3-propanediol, 3-methyl-1,5-pentanediol, hexylene glycol (2-methyl-2,4-pentanediol), 3-methyl-1,3,5-pentanetriol and 1,2,4-butanetriol, alone or as mixtures.

The at least one polyol of the formula (I) disclosed herein may be present in an amount ranging, for example, from 0.01% to 30% by weight, such as from 0.1% to 20% by weight and further such as from 0.5% to 10% by weight, relative to the total weight of the composition.

The composition also comprises at least one fluorescent dye.

As used herein, the term "fluorescent dye" means a dye which is a molecule that colors by itself, and thus absorbs light in the visible spectrum and possibly in the ultraviolet spectrum (wavelengths ranging from 360 to 760 nanometers), but which, in contrast with a standard dye, converts the absorbed energy into fluorescent light of a longer wavelength emitted in the visible region of the spectrum.

A fluorescent dye as disclosed herein is to be differentiated from an optical brightener. Optical brighteners, which are also known as brighteners, fluorescent brighteners, fluorescent brightening agents, fluorescent whitening agents, whiteners or fluorescent whiteners, are colorless transparent compounds, which do not dye because they do not absorb light in the visible region, but only in the ultraviolet region (wavelengths ranging from 200 to 400 nanometers), and convert the absorbed energy into fluorescent light of a longer wavelength emitted in the visible region of the spectrum; the color impression is then generated solely by purely fluorescent light that is predominantly blue (wavelengths ranging from 400 to 500 nanometers).

Finally, the fluorescent dye used in the composition is soluble in the medium of the composition. It should be pointed out that the fluorescent dye differs therein from a fluorescent pigment, which itself is insoluble in the medium of the composition.

In one embodiment, the fluorescent dye as disclosed herein, which is optionally neutralized, is soluble in the medium of the composition to at least 0.001 g/l, such as at least 0.5 g/l, further such as at least 1 g/l and, and even further such as at least 5 g/l at a temperature ranging from 15 to 25° C.

Moreover, as disclosed herein, the composition does not comprise, as a fluorescent dye, 2-[2-(4-dialkylamino)phenylethenyl]-1-alkylpyridinium wherein the alkyl radical of the pyridinium nucleus is a methyl or ethyl radical, the alkyl radical of the benzene nucleus is a methyl radical, and the counterion is a halide.

In one embodiment, the composition does not comprise, as a fluorescent dye, a compound chosen from azo, azomethine and methine monocationic heterocyclic fluorescent dyes.

The fluorescent dyes disclosed herein are, for example, chosen from dyes in the orange range.

In one embodiment, the fluorescent dyes disclosed herein lead to a reflectance maximum that is in the wavelength range from 500 to 650 nanometers such as in the wavelength range from 550 to 620 nanometers.

Some of the fluorescent dyes disclosed herein are compounds that are known per se.

As examples of fluorescent dyes that may be used, mention may be made, for example, of the fluorescent dyes belonging to the following families: naphthalimides; cationic and non-cationic coumarins; xanthenodiquinolizines (such as sulphorhodamines); azaxanthenes; naphtholactams; azlactones; oxazines; thiazines; dioxazines; polycationic fluorescent dyes of azo, azomethine and methine types, alone or as mixtures. For example, the fluorescent dyes of the following families can be used: naphthalimides; cationic and non-cationic coumarins; azaxanthenes; naphtholactams; azlactones; oxazines; thiazines; dioxazines; polycationic fluorescent dyes of azo, azomethine and methine types, alone or as mixtures.

Further, for example, the following may be mentioned among the fluorescent dyes:

Brilliant Yellow B6GL sold by the company Sandoz and having the following formula (F1):

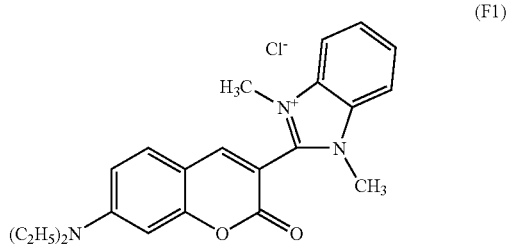

Basic Yellow 2, or Auramine O, sold by the companies Prolabo, Aldrich or Carlo Erba and having the following formula (F2):

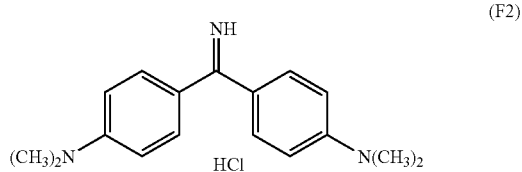

4,4'-(imidocarbonyl)bis(N,N-dimethylaniline)monohydrochloride—CAS number 2465-27-2.

Mention may also be made of the compounds having the following formula (F3):

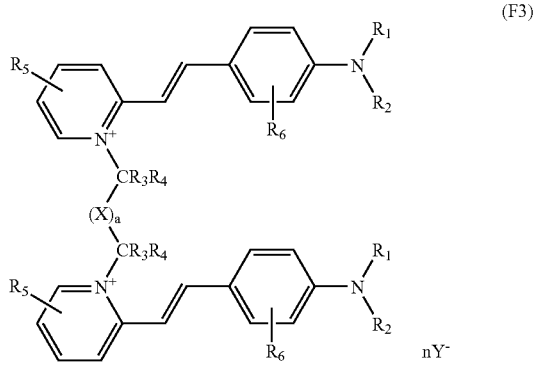

wherein:

$R_1$ and $R_2$, which may be identical or different, are each chosen from:
a hydrogen atom;
linear and branched alkyl radicals comprising from 1 to 10 carbon atoms, such as from 1 to 4 carbon atoms, optionally interrupted and/or substituted with at least one entity chosen from hetero atoms and groups comprising at least one hetero atom and/or optionally substituted with at least one halogen. atom;
aryl and arylalkyl radicals, wherein the aryl group comprises 6 carbon atoms and the alkyl radical comprises from 1 to 4 carbon atoms; the aryl radical is optionally substituted with at least one alkyl radical chosen from linear and branched alkyl radicals comprising 1 to 4 carbon atoms optionally interrupted and/or substituted with at least one entity chosen from hetero atoms and groups comprising at least one hetero atom and/or optionally substituted with at least one halogen atom;
$R_1$ and $R_2$ may optionally be linked so as to form a heterocycle with the nitrogen atom and may comprise at least one other hetero atom, wherein the heterocycle is optionally substituted with at least one alkyl radical chosen from linear and branched alkyl radicals comprising, for example, from 1 to 4 carbon atoms, and optionally being interrupted and/or substituted with at least one entity chosen from hetero atoms and groups comprising at least one hetero atom and/or optionally substituted with at least one halogen atom; and
$R_1$ or $R_2$ may optionally be engaged in a heterocycle comprising the nitrogen atom and one of the carbon atoms of the phenyl group bearing the nitrogen atom;
$R_3$ and $R_4$, which may be identical or different, are each chosen from a hydrogen atom and alkyl radicals comprising from 1 to 4 carbon atoms;
$R_5$, which may be identical or different, are each chosen from a hydrogen atom, halogen atoms, and linear and branched alkyl radicals comprising from 1 to 4 carbon atoms, optionally interrupted with at least one hetero atom;
$R_6$, which may be identical or different, are each chosen from a hydrogen atom; halogen atoms; linear and branched alkyl radicals comprising from 1 to 4 carbon atoms, optionally substituted and/or interrupted with at least one entity chosen from hetero atoms and groups bearing at least one hetero atom and/or optionally substituted with at least one halogen atom;
X is chosen from:
linear and branched alkyl radicals comprising from 1 to 14 carbon atoms and alkenyl radicals comprising from 2 to 14 carbon atoms, optionally interrupted and/or substituted with at least one entity chosen from hetero atoms and groups comprising at least one hetero atom and/or optionally substituted with at least one halogen atom;
5- and 6-membered heterocyclic radicals optionally substituted with at least one alkyl radical chosen from linear and branched alkyl radicals comprising from 1 to 14 carbon atoms, optionally substituted with at least one hetero atom; optionally substituted with at least one aminoalkyl radical chosen from linear and branched aminoalkyl radicals comprising from 1 to 4 carbon atoms, optionally substituted with at least one hetero atom; and optionally substituted with at least one halogen atom;
fused and non-fused, aromatic and diaromatic radicals, optionally separated with at least one alkyl radical chosen from alkyl radicals comprising from 1 to 4 carbon atoms, wherein at least one of the aryl radicals is optionally substituted with at least one halogen atom or with at least one alkyl radical chosen from alkyl radicals comprising from 1 to 10 carbon atoms optionally substituted and/or interrupted with at least one entity chosen from hetero atoms and groups bearing at least one hetero atom; and a dicarbonyl radical;

provided that the group X possibly bears at least one cationic charge;

a is equal to 0 or 1;

$Y^-$, which may be identical or different, are each an anion chosen from organic and mineral anions; and n is an integer at least equal to 2 and at most equal to the number of cationic charges present in the fluorescent compound.

As used herein, the term "hetero atom" is an oxygen or nitrogen atom.

Among the groups bearing such hetero atoms that may be mentioned, inter alia, are hydroxyl, alkoxy, carbonyl, amino, ammonium, amido (—N—CO—) and carboxyl (—O—CO— or —CO—O—) groups.

With regard to the alkenyl groups, they comprise at least one unsaturated carbon-carbon bond (—C=C—). In one embodiment, they comprise only one carbon-carbon double bond.

In the formula (F3), the radicals $R_1$ and $R_2$, which may be identical or different, are chosen, for example, from:

a hydrogen atom;

alkyl radicals comprising from 1 to 10 carbon atoms, such as from 1 to 6 carbon atoms, and further such as from 1 to 4 carbon atoms, optionally interrupted with an oxygen atom or optionally substituted with at least one entity chosen from hydroxyl, amino and ammonium radicals and chlorine and fluorine atoms;

benzyl and phenyl radicals optionally substituted with at least one radical chosen from alkyl and alkoxy radicals comprising from 1 to 4 carbon atoms, such as from 1 to 2 carbon atoms;

with the nitrogen atom, a heterocyclic radical of the pyrrolo, pyrrolidino, imidazolino, imidazolo, imidazolium, pyrazolino, piperazino, morpholino, morpholo, pyrazolo or triazolo type, optionally substituted with at least one radical chosen from linear and branched alkyl radicals comprising from 1 to 4 carbon atoms optionally interrupted and/or substituted with at least one entity chosen from nitrogen and oxygen atoms and groups bearing at least one atom chosen from nitrogen and oxygen atoms.

With regard to the above-mentioned amino or ammonium radicals, the radicals borne by the nitrogen atom may be identical or different and may, for example, be chosen from a hydrogen atom, $C_1-C_{10}$ alkyl radicals, such as $C_1-C_4$ alkyl radicals, and arylalkyl radicals wherein, for example, the aryl radical comprises 6 carbon atoms and the alkyl radical comprises from 1 to 10 carbon atoms, such as from 1 to 4 carbon atoms.

In one embodiment, the radicals $R_1$ and $R_2$, which may be identical or different, are each chosen from a hydrogen atom; linear and branched $C_1-C_6$ alkyl radicals; $C_2-C_6$ alkyl radicals substituted with at least one hydroxyl radical; $C_2-C_6$ alkyl radicals bearing at least one group chosen from amino and ammonium groups; $C_2-C_6$ chloroalkyl radicals; $C_2-C_6$ alkyl radicals interrupted with at least one entity chosen from an oxygen atom and groups bearing at least one oxygen atom (for example, ester); aromatic radicals, for instance phenyl, benzyl and 4-methylphenyl radicals; heterocyclic radicals such as pyrrolo, pyrrolidino, imidazolo, imidazolino, imidazolium, piperazino, morpholo, morpholino, pyrazolo and triazolo radicals, optionally substituted with at least one radical chosen from $C_1-C_6$ alkyl and aromatic radicals.

In another embodiment, the radicals $R_1$ and $R_2$, which may be identical or different, are each chosen from a hydrogen atom, linear and branched $C_1-C_6$ alkyl radicals such as methyl, ethyl, n-butyl and n-propyl radicals; 2-hydroxyethyl radicals; alkyltrimethylammonium and alkyltriethylammonium radicals, wherein the alkyl radical is chosen from linear $C_2-C_6$ alkyl radicals; (di)alkylmethylamino and (di)alkylethylamino radicals, wherein the alkyl radical is chosen from linear $C_1-C_6$ alkyl radicals; —$CH_2CH_2Cl$; —$(CH_2)_n$—$OCH_3$ and —$(CH_2)_n$—$OCH_2CH_3$ wherein n is an integer ranging from 2 to 6; —$CH_2CH_2$—$OCOCH_3$; and —$CH_2CH_2COOCH_3$.

In yet another embodiment, the radicals $R_1$ and $R_2$, which are identical or different, (which are, for example, identical), are chosen from a methyl radical and an ethyl radical.

The radicals $R_1$ and $R_2$, which may be identical or different, may also be chosen from heterocyclic radicals of the pyrrolidino, 3-aminopyrrolidino, 3-(dimethyl)-aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo and 1H-1,2,4-triazolo types.

The radicals $R_1$ and $R_2$, which may be identical or different, may also be chosen and be linked so as to form a heterocycle chosen from heterocylces of formulae (I) and (II) below:

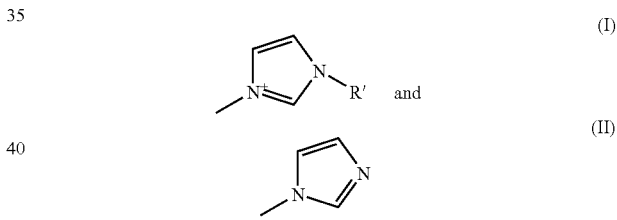

wherein R' is chosen from a hydrogen atom, $C_1-C_3$ alkyl radicals, —$CH_2CH_2OH$, and —$CH_2CH_2OCH_3$.

In one embodiment, $R_5$, which may be identical or different, are each chosen from a hydrogen atom, fluorine and chlorine atoms, linear and branched alkyl radicals comprising from 1 to 4 carbon atoms optionally interrupted with at least one atom chosen from oxygen and nitrogen atoms.

The substituent $R_5$, if it is other than hydrogen, is, for example, in a position chosen from positions 3 and 5 relative to the carbon of the ring bearing the nitrogen substituted with the radicals $R_1$ and $R_2$. In one embodiment, the substituent $R_5$ is in position 3 relative to that carbon.

For example, the radicals $R_5$, which may be identical or different, are each chosen from a hydrogen atom; linear and branched $C_1-C_4$ alkyl radicals; —O—$R_{51}$ radicals wherein $R_{51}$ is chosen from linear $C_1-C_4$ alkyl radicals; —$R_{52}$—O—$CH_3$ radicals wherein $R_{52}$ is chosen from linear $C_2-C_3$ alkyl radicals; —$R_{53}$—$N(R_{54})_2$ radicals wherein $R_{53}$ is chosen from linear $C_2-C_3$ alkyl radicals and $R_{54}$, which may be identical or different, are each chosen from a hydrogen atom and a methyl radical.

Further, for example, $R_5$, which may be identical or different, are each chosen from hydrogen, and methyl and methoxy radicals. In one embodiment, $R_5$ is a hydrogen atom.

In another embodiment, the radicals $R_6$, which may be identical or different, are each chosen from a hydrogen atom; linear and branched $C_1$–$C_4$ alkyl radicals; —X' radicals wherein X' is chosen from chlorine, bromine and fluorine atoms; —$R_{61}$—O—$R_{62}$ radicals wherein $R_{61}$ is chosen from linear $C_2$–$C_3$ alkyl radicals and $R_{62}$ is a methyl radical; —$R_{63}$—N($R_{64}$)$_2$ radicals wherein $R_{63}$ is chosen from linear $C_2$–$C_3$ alkyl radicals and $R_{64}$, which may be identical or different, are each chosen from a hydrogen atom and a methyl radical; —N($R_{65}$)$_2$ radicals wherein $R_{65}$, which may be identical or different, are each chosen from a hydrogen atom and linear $C_2$–$C_3$ alkyl radicals; —NHCOR$_{66}$ radicals wherein $R_{66}$ is chosen from $C_1$–$C_2$ alkyl radicals, $C_1$–$C_2$ chloroalkyl radicals, radicals —$R_{67}$—NH$_2$, —$R_{67}$—NH(CH$_3$), —$R_{67}$—N(CH$_3$)$_2$, —$R_{67}$—N$^+$(CH$_3$)$_3$, and —$R_{67}$—N$^+$(CH$_2$CH$_3$)$_3$ wherein $R_{67}$ is chosen from $C_1$–$C_2$ alkyl radicals.

The substituent $R_6$, if it is other than hydrogen, is, for example, in a position chosen from positions 2 and 4 relative to the nitrogen atom of the pyridinium ring. In one embodiment, the substituent $R_6$ is in position 4 relative to that nitrogen atom.

For example, these radicals $R_6$, which may be identical or different, are each chosen from a hydrogen atom and methyl and ethyl radicals. In one embodiment, $R_6$ is a hydrogen atom.

The radicals $R_3$ and $R_4$, which may be identical or different, are each chosen, for example, from a hydrogen atom and alkyl radicals comprising from 1 to 4 carbon atoms, such as a methyl radical. In one embodiment, $R_3$ and $R_4$ are each a hydrogen atom.

As mentioned above, X is chosen, for example, from:
linear and branched alkyl radicals comprising from 1 to 14 carbon atoms and alkenyl radicals comprising 2 to 14 carbon atoms, optionally interrupted and/or substituted with at least one entity chosen from hetero atoms and groups bearing at least one hetero atom and/or optionally substituted with at least one halogen atom;
5- and 6-membered heterocyclic radicals optionally substituted with at least one alkyl radical chosen from linear and branched alkyl radicals comprising from 1 to 14 carbon atoms; optionally substituted with at least one aminoalkyl radical chosen from linear and branched aminoalkyl radicals comprising from 1 to 4 carbon atoms, optionally substituted with at least one hetero atom; and optionally substituted with at least one halogen atom;
fused and non-fused, aromatic and diaromatic radicals, optionally separated with at least one alkyl radical chosen from alkyl radicals comprising from 1 to 4 carbon atoms, wherein at least one of the aryl radicals is optionally substituted with at least one halogen atom or with at least one alkyl radical chosen from alkyl radicals comprising from 1 to 10 carbon atoms optionally substituted and/or interrupted with at least one entity chosen from hetero atoms and groups bearing at least one hetero atom; and
a dicarbonyl radical.

In addition, the group X may bear at least one cationic charge.

Thus, X may be chosen from linear and branched alkyl radicals comprising from 1 to 14 carbon atoms and alkenyl radicals comprising from 2 to 14 carbon atoms, may be substituted and/or interrupted with at least one entity chosen from oxygen and nitrogen atoms and groups bearing at least one hetero atom, and may be substituted with at least one atom chosen from fluorine and chlorine atoms.

Among the groups of this type that may be mentioned, for example, are hydroxyl, alkoxy (such as with a radical R of the $C_1$–$C_4$ alkyl type), amino, ammonium, amido, carbonyl and carboxyl groups (—COO— or —O—CO—) such as with a radical of alkyloxy type.

The nitrogen atom, if present, may be in a quaternized or non-quaternized form. In this case, the other radical or the other two radicals borne by the quaternized or non-quaternized nitrogen atom may be identical or different and may be chosen from a hydrogen atom and $C_1$–$C_4$ alkyl radicals, such as a methyl radical.

In one embodiment, the group X is chosen from 5- and 6-membered heterocyclic radicals of the imidazolo, pyrazolo, triazino and pyridino types, optionally substituted with at least one alkyl radical chosen from linear and branched alkyl radicals comprising from 1 to 14 carbon atoms, such as from 1 to 10 carbon atoms, and further such as from 1 to 4 carbon atoms; optionally substituted with at least one aminoalkyl radical chosen from linear and branched aminoalkyl radicals comprising from 1 to 10 carbon atoms, such as from 1 to 4 carbon atoms, optionally substituted with at least one entity chosen from groups comprising at least one hetero atom (such as a hydroxyl radical); and optionally substituted with at least one halogen atom. The amino group can, for example, be linked to the heterocycle.

In another embodiment, the group X is chosen from aromatic radicals comprising, for example, 6 carbon atoms, and fused and non-fused diaromatic radicals comprising, for example, from 10 to 12 carbon atoms, possibly separated with at least one alkyl radical chosen from alkyl radicals comprising from 1 to 4 carbon atoms, wherein at least one of the aryl radicals is optionally substituted with at least one entity chosen from halogen atoms and alkyl radicals comprising from 1 to 10 carbon atoms, such as from 1 to 4 carbon atoms, optionally interrupted with at least one entity chosen from oxygen and nitrogen atoms and groups comprising at least one hetero atom, for example, carbonyl, carboxyl, amido, amino and ammonium radicals.

The aromatic radical, such as a phenyl radical, is linked to the groups CR$_3$R$_4$ via bonds in positions 1,2, 1,3 or 1,4 such as in positions 1,3 and 1,4. If the phenyl radical linked via bonds in positions 1,4 bears one or two substituents, this or these substituent(s) is(are), for example, located in position 1,4 relative to one of the groups CR$_3$R$_4$. If the phenyl radical linked via bonds in positions 1,3 bears one or two substituents, this or these substituent(s) is (are), for example, located in position 1 and/or 3 relative to one of the groups CR$_3$R$_4$.

In the case where the radical is diaromatic, it is, for example, non-fused and comprises two phenyl radicals possibly separated with a single bond (i.e., a carbon of each of the two rings) or with an alkyl radical, such as of CH$_2$ or C(CH$_3$)$_2$ type. In one embodiment, the aromatic radicals do not bear a substituent. It should be noted that the diaromatic radical is linked to the groups CR$_3$R$_4$ via bonds in positions 4,4'.

The groups X that are suitable may be chosen, for example, from linear and branched alkyl radicals comprising from 1 to 13 carbon atoms, such as methylene, ethylene, propylene, isopropylene, n-butylene, pentylene and hexylene; 2-hydroxypropylene and 2-hydroxy-n-butylene; $C_1$–$C_{13}$ alkylene radicals substituted or interrupted with at least one entity chosen from nitrogen and oxygen atoms, and groups bearing at least one hetero atom (for example, hydroxyl, amino, ammonium, carbonyl and carboxyl radicals), such as —CH$_2$CH$_2$OCH$_2$CH$_2$—, 1,6-dideoxy-d-mannitol, —CH$_2$N$^+$(CH$_3$)$_2$CH$_2$—, —CH$_2$CH$_2$N$^+$(CH$_3$)$_2$—(CH$_2$)$_6$N$^+$(CH$_3$)$_2$—CH$_2$CH$_2$—, CO—CO—, 3,3-dimethylpentylene 2-acetoxyethylene, butylene-1,2,3,4-tetraol; —CH═CH—; aromatic and diaromatic radicals substituted with at least one entity chosen from alkyl radicals, groups bearing at least one hetero atom, and halogen atoms, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate and 1,4-bis(amidomethyl)phenyl; radicals of heterocyclic type such as pyridine, and derivatives thereof such as 2,6-bispyridine, imidazole, imidazolium and triazine.

In one embodiment, X is chosen from linear and branched C$_1$–C$_{13}$ alkyl radicals; —CH$_2$CH(OH)CH$_2$—; —CH$_2$CH(Cl)CH$_2$—; —CH$_2$CH$_2$—OCOCH$_2$—; —CH$_2$CH$_2$COOCH$_2$—; —Ra—O—Rb— radicals wherein Ra is chosen from linear C$_2$–C$_6$ alkyl radicals and Rb is chosen from C$_1$–C$_2$ alkyl radicals; —Rc-N(Rd)—Re— radicals wherein Rc is chosen from C$_2$–C$_9$ alkyl radicals, Rd is chosen from a hydrogen atom and C$_1$–C$_2$ alkyl radicals, and Re is chosen from C$_1$–C$_6$ alkyl radicals; —Rf—N$^+$(Rg)$_2$-Rh— radicals wherein Rf is chosen from linear C$_2$–C$_9$ alkyl radicals, Rg, which may be identical or different, (for example, which are identical), are each chosen from C$_1$–C$_2$ alkyl radicals and Rh is chosen from linear C$_1$–C$_6$ alkyl radicals; and —CO—CO—.

X may furthermore be chosen, for example, from imidazole radicals optionally substituted with at least one alkyl radical chosen from alkyl radicals comprising from 1 to 14 carbon atoms, such as from 1 to 10 carbon atoms, and further such as from 1 to 4 carbon atoms, and for example the divalent radicals having the following formula (III):

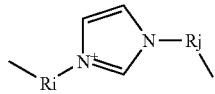
(III)

wherein Ri and Rj, which may be identical or different, are each chosen from linear C$_1$–C$_6$ alkyl radicals;

X may similarly be chosen, for example, from the divalent triazine-based radicals below:

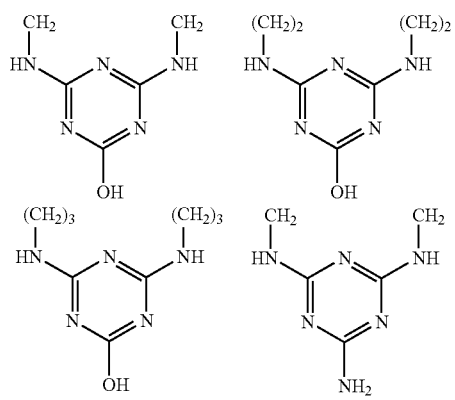

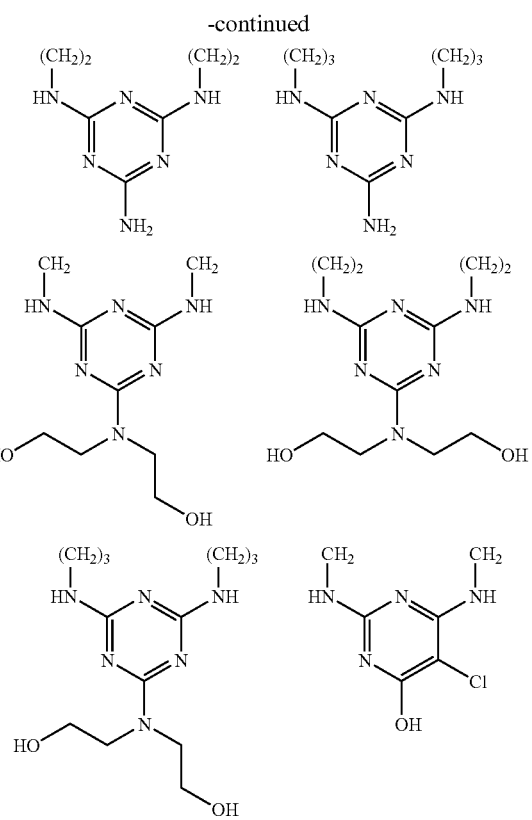

In one embodiment, X may be chosen from the divalent aromatic radicals below:

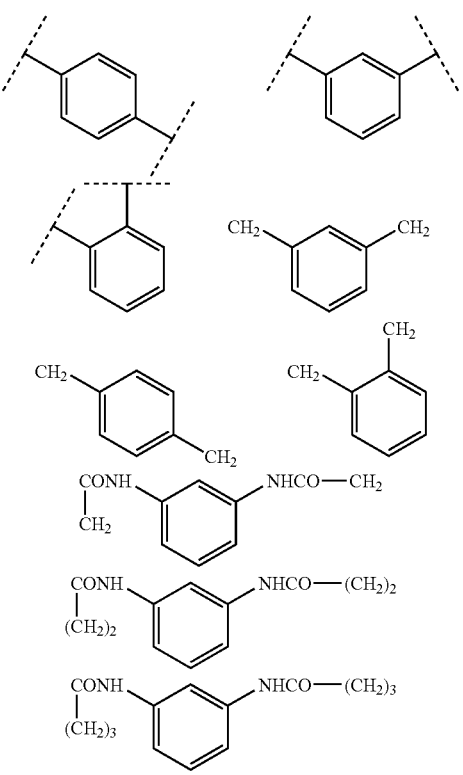

-continued

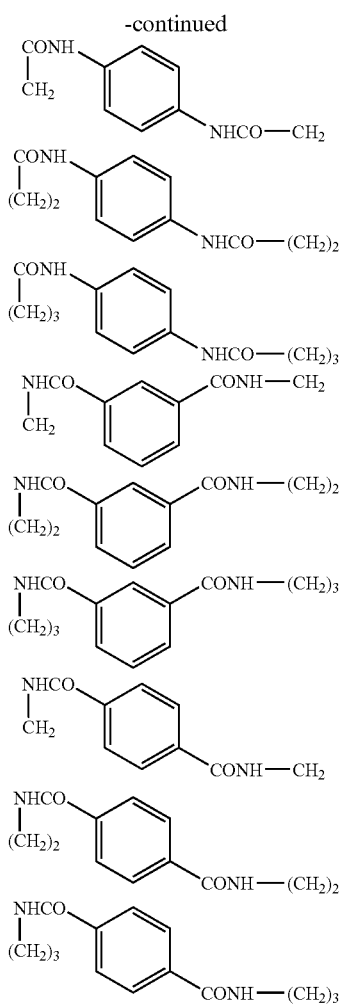

In the formula (F3) of the fluorescent compounds, Y⁻ is an anion chosen from organic and mineral anions. If there are several anions Y⁻, these anions may be identical or different.

Among the anions of mineral origin that may be mentioned, examples include anions derived from halogen atoms, such as chlorides, iodides, sulphates and bisulphates, nitrates, phosphates, hydrogen phosphates, dihydrogen phosphates, carbonates and bicarbonates.

Among the anions of organic origin that may be mentioned, examples include anions derived from the salts of saturated or unsaturated, aromatic or non-aromatic monocarboxylic or polycarboxylic, sulphonic or sulphuric acids, optionally substituted with at least one entity chosen from hydroxyl and amino radicals and halogen atoms. Non-limiting examples that are suitable for use include acetates, hydroxyacetates, aminoacetates, (tri)chloroacetates, benzoxyacetates, propionates and derivatives bearing at least one chlorine atom, fumarates, oxalates, acrylates, malonates, succinates, lactates, tartrates, glycolates, citrates, benzoates and derivatives bearing at least one radical chosen from methyl and amino radicals, alkyl sulphates, tosylates, benzenesulphonates, toluene-sulphonates, etc.

In one embodiment, Y⁻, which may be identical or different, are each chosen from chloride, sulphate, methosulphate and ethosulphate.

Finally, the integer n is at least equal to 2 and at most equal to the number of cationic charges present in the fluorescent compound.

For example, the fluorescent compounds that have just been described in detail are symmetrical compounds.

These compounds may be synthesized by reacting, in a first step, α-picoline with a reagent comprising two leaving groups that may be chosen from halogen atoms, such as bromine and chlorine, or groups of tolylsulphonyl or methanesulphonyl type.

This first step may take place in the presence of a solvent, for example, dimethylformamide.

The number of moles of α-picoline is generally in the range of 2 per mole of reagent comprising the leaving groups.

In addition, the reaction is usually performed at the reflux temperature of the reagent and/or of the solvent if a solvent is present.

The product derived from this first step is then placed in contact with a corresponding aldehyde having the following formula:

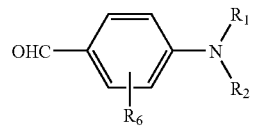

wherein $R_1$, $R_2$ and $R_6$ have the same meanings as indicated above in the formula (F3).

In this case, the reaction may be performed in the presence of a suitable solvent, which is, for example, at reflux.

The radicals $R_1$ and $R_2$ of the aldehyde may have the meaning indicated in the formula (F3) described previously.

It is also possible to use an aldehyde wherein the radicals $R_1$, $R_2$ and $R_6$ are each a hydrogen atom and to perform, in accordance with standard methods, the substitution of these hydrogen atoms with suitable radicals as described in the general formula once the second step is complete.

Reference may be made, for example, to syntheses as described in U.S. Pat. No. 4,256,458.

The at least one fluorescent dye present in the composition disclosed herein may be present in an amount ranging, for example, from 0.01% to 20% by weight, such as from 0.05% to 10% by weight, and further such as from 0.1% to 5% by weight, relative to the total weight of the composition.

The cosmetically acceptable medium generally comprises water or a mixture of water and at least one organic solvent chosen from common organic solvents.

Among the solvents that are suitable for use, mention may be made, for example, of alcohols such as ethyl alcohol, isopropyl alcohol, benzyl alcohol and phenylethyl alcohol, glycols and glycol ethers, for instance ethylene glycol monomethyl ether, monoethyl ether and monobutyl ether, propylene glycol and ethers thereof, for instance propylene glycol monomethyl ether, butylene glycol, dipropylene glycol and diethylene glycol alkyl ethers, for instance diethylene glycol monoethyl ether and monobutyl ether, and polyols, for instance glycerol. Polyethylene glycols and polypropylene glycols, and mixtures of all these compounds, may also be used.

The at least one organic solvent, if present, is in an amount ranging, for example, from 1% to 40% by weight, such as from 5% to 30% by weight, relative to the total weight of the composition.

The pH of the composition disclosed herein ranges, for example, from 3 to 12, such as from 5 to 11.

The pH may be adjusted to the desired value by means of acidifying or basifying agents commonly used in the field such as in the dyeing of human keratin fibers.

Examples of acidifying agents that may be mentioned include mineral or organic acids, for instance hydrochloric acid, orthophosphoric acid, sulphuric acid, carboxylic acids, for instance acetic acid, tartaric acid, citric acid and lactic acid, and sulphonic acids.

Examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (A) below:

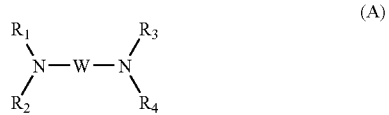

wherein W is a propylene residue optionally substituted with at least one entity chosen from a hydroxyl group and $C_1$–$C_6$ alkyl radicals; $R_1$, $R_2$, $R_3$ and $R_4$, which may be identical or different, are each chosen from a hydrogen atom and $C_1$–$C_6$ alkyl and $C_1$–$C_6$ hydroxyalkyl radicals.

In one embodiment, the composition may comprise, in addition to the at least one fluorescent dye, at least one additional non-fluorescent direct dye chosen from direct dyes of nonionic, cationic and anionic nature, which may be chosen, for example, from nitrobenzene dyes.

The following red or orange nitrobenzene direct dyes are, for example, suitable for use:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl) aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The composition disclosed herein may also comprise, in addition to or in replacement for these nitrobenzene dyes, at least one additional direct dye chosen from yellow, green-yellow, blue and violet nitrobenzene dyes, azo dyes, anthraquinone dyes, naphthoquinone dyes, benzoquinone dyes, indigoid dyes, and triarylmethane-based dyes.

The at least one additional direct dye may be chosen, for example, from basic dyes, among which mention may be made, for example, of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", and acidic direct dyes, among which mention may be made, for example, of the dyes known in the Color Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", and cationic direct dyes such as those described in patent applications WO 95/01772, WO 95/15144 and EP-A-0 714 954.

Among the additional yellow and green-yellow nitrobenzene direct dyes that may be mentioned, for example, are the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue or violet nitrobenzene direct dyes that may be mentioned, for example, are the compounds chosen from:
1-(β-hydroxyethyl)amino-4-N,N-bis(β-hydroxyethyl) amino-2-nitrobenzene,
1-(γ-hydroxypropyl)amino-4,N,N-bis(β-hydroxyethyl) amino-2-nitrobenzene,
1-(β-hydroxyethyl)amino-4-(N-methyl-N-β-hydroxyethyl) amino-2-nitrobenzene,
1-(β-hydroxyethyl)amino-4-(N-ethyl-N-β-hydroxyethyl) amino-2-nitrobenzene,
1-(β,γ-dihydroxypropyl)amino-4-(N-ethyl-N-β-hydroxyethyl)amino-2-nitrobenzene, and
2-nitroparaphenylenediamines having the following formula:

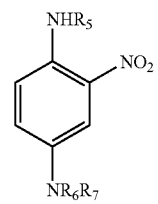

wherein:

R$_6$ is chosen from C$_1$–C$_4$ alkyl radicals and β-hydroxyethyl, β-hydroxypropyl and γ-hydroxypropyl radicals;

—R$_5$ and R$_7$, which may be identical or different, are each chosen from β-hydroxyethyl, β-hydroxypropyl, γ-hydroxypropyl and β,γ-dihydroxypropyl radicals, provided that at least one of the radicals chosen from R$_5$, R$_6$ and R$_7$ is a γ-hydroxypropyl radical and R$_6$ and R$_7$ are not simultaneously able to be a β-hydroxyethyl radical when R$_6$ is a γ-hydroxypropyl radical, such as those described in French Patent No. 2 692 572.

When present, the at least one additional direct dye is in an amount ranging, for example, from 0.0005% to 12% by weight, such as from 0.005% to 6% by weight, relative to the total weight of the composition.

When it is intended for oxidation dyeing, the composition disclosed herein comprises, in addition to the at least one fluorescent dye, at least one oxidation base chosen from the oxidation bases conventionally used for oxidation dyeing and among which mention may be made, for example, of para-phenylenediamines, bis(phenyl)alkylenediamines, para-aminophenols, ortho-aminophenols and heterocyclic bases, and the acid or base addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the acid or base addition salts thereof.

Among the para-phenylenediamines mentioned above, examples include para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid or base addition salts thereof.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,5-dioxaoctane, and the acid or base addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid or base addition salts thereof.

Among the ortho-aminophenols that may be mentioned, for example, are 2-aminophenol, 2-amino-5-methylphenol, 2-amino-6-methylphenol and 5-acetamido-2-aminophenol, and the acid or base addition salts thereof.

Among the heterocyclic bases that may be mentioned, for example, are pyridine derivatives, pyrimidine derivatives and pyrazole derivatives, and the acid or base addition salts thereof.

When used, the at least one oxidation base is present in an amount ranging, for example, from 0.0005% to 12% by weight, such as from 0.005% to 6% by weight, relative to the total weight of the composition.

When it is intended for oxidation dyeing, the composition disclosed herein may also comprise, in addition to the at least one fluorescent dye and the at least one oxidation base, at least one coupler so as to modify or to enrich with glints the shades obtained using the at least one fluorescent dye and the at least one oxidation base.

The couplers that may be used in the composition disclosed herein may be chosen from the couplers conventionally used in oxidation dyeing, and among which mention may be made, for example, of meta-phenylenediamines, meta-aminophenols, meta-diphenols and heterocyclic couplers, and the acid or base addition salts thereof.

These couplers are, for example, chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridin 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the acid and base addition salts thereof.

If present, the at least one coupler is present in an amount ranging, for example, from 0.0001% to 10% by weight, such as from 0.005% to 5% by weight, relative to the total weight of the composition.

In general, the acid addition salts that may be used in the context of the composition disclosed herein (oxidation bases and couplers) are chosen, for example, from hydrochlorides, hydrobromides, sulphates, citrates, succinates, tartrates, tosylates, benzenesulphonates, lactates and acetates.

The base addition salts that may be used in the context of the composition disclosed herein (oxidation bases and couplers) are chosen, for example, from the addition salts with alkali metals, alkaline-earth metals, ammonia and organic amines, including alkanolamines and the compounds of formula (A).

The composition disclosed herein may also comprise at least one adjuvant chosen from various conventionally used adjuvants, such as anionic, cationic, nonionic, amphoteric and zwitterionic surfactants and mixtures thereof, anionic, cationic, nonionic, amphoteric and zwitterionic polymers and mixtures thereof, mineral and organic thickeners, antioxidants, penetrating agents, sequestering agents, fragrances, buffers, dispersants, conditioners, for instance cations, cationic and amphoteric polymers, volatile and nonvolatile, modified and unmodified silicones, film-forming agents, ceramides, preserving agents, stabilizers and opacifiers.

Among the thickeners, thickening systems based on associative polymers that are well known to those skilled in the art may, for example, be used, such as those of nonionic, anionic, cationic or amphoteric nature.

When at least one surfactant is present, chosen, for example, from those of nonionic, anionic and amphoteric types, the at least one surfactant is in an amount ranging, for example, from 0.01% to 30% by weight relative to the weight of the composition.

Needless to say, a person skilled in the art will take care to select this or these optional additional compound(s) such that the advantageous properties intrinsically associated with the composition disclosed herein are not, or are not substantially, adversely affected by the envisaged addition(s).

The composition disclosed herein may be in various forms, such as in the form of liquids, shampoos, creams or gels, or in any other suitable form.

In one embodiment, the composition disclosed herein is in the form of a lightening dye shampoo.

In the composition disclosed herein, when at least one oxidation base is used, optionally in the presence of at least one coupler, or when the at least one fluorescent dye is used in the context of a lightening direct dyeing, then the composition disclosed herein may also comprise at least one oxidizing agent chosen, for example, from hydrogen peroxide, urea peroxide, alkali metal bromates, persalts such as perborates and persulphates, and enzymes such as peroxidases and two-electron or four-electron oxidoreductases. In one embodiment, the at least one oxidizing agent is chosen from hydrogen peroxide and enzymes.

Further disclosed herein is the use of a composition for dyeing a human keratin material with a lightening effect, wherein the composition comprises, in a cosmetically acceptable medium, at least one fluorescent dye that is soluble in the medium, and at least one polyol with a molecular weight of less than 500 g/mol and comprising more than three carbon atoms, of formula (I) below:

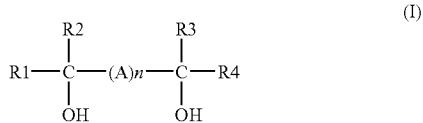

wherein:

A is a divalent radical of a hydrocarbon-based chain chosen from linear and branched, saturated and unsaturated hydrocarbon-based chains, optionally interrupted with from 2 to 10 hetero atoms and comprising from 1 to 35 carbon atoms, $R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and n is 0 or 1.

In the context of this use, the at least one fluorescent dye may be chosen from the fluorescent compounds belonging to the following families: naphthalimides; cationic and non-cationic coumarins; xanthenodiquinolizines (such as sulphorhodamines); azaxanthenes; naphtholactams; azlactones; oxazines; thiazines; dioxazines; monocationic and polycationic fluorescent dyes of azo, azomethine and methine types, alone or as mixtures.

For example, compounds of the formulae F1, F2 and F3 already described above may be used.

It is similarly possible to use the compounds of formula (F4) below:

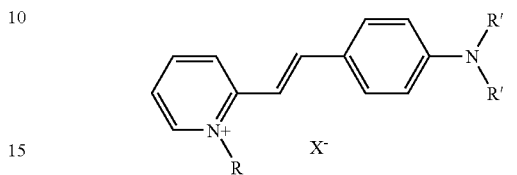

wherein R is chosen from methyl and ethyl radicals; R' is a methyl radical and $X^-$ is an anion such as chloride, iodide, sulphate, methosulphate, acetate and perchlorate. An example of a compound of this type that may be mentioned is the Photosensitizing Dye NK-557 sold by the company Ubichem, wherein R is an ethyl radical, R' is a methyl radical and $X^-$ is an iodide.

Everything that has been described previously regarding the natures and contents of the various additives present in the composition remains valid and will not be repeated in this section.

As used herein, the term "human keratin materials" includes the skin, the hair, the nails, the eyelashes and the eyebrows, such as dark skin and artificially colored or pigmented hair.

Further as used herein, the term "dark skin" means a skin whose lightness L* measured in the CIEL L*a*b* system is less than or equal to 45, such as less than or equal to 40, given that L*=0 is equivalent to black and L*=100 is equivalent to white. The skin types corresponding to this lightness are, for example, African skin, afro-American skin, hispano-American skin, Indian skin and North African skin.

As used herein, the term "artificially dyed or pigmented hair" means hair whose tone height is less than or equal to 6 (dark blond) such as less than or equal to 4 (chestnut-brown).

The lightening of the hair is evaluated by the "tone height," which characterizes the degree or level of lightening. The notion of "tone" is based on the classification of the natural shades, one tone separating each shade from the shade immediately following or preceding it. This definition and the classification of the natural shades are well known to hairstyling professionals and are published in the book "Sciences des traitements capillaires [Hair treatment sciences]" by Charles Zviak, 1988, published by Masson, pp. 215 and 278.

The tone heights range from 1 (black) to 10 (light blond), one unit corresponding to one tone; the higher the figure, the lighter the shade.

Further disclosed herein is a process for dyeing keratin fibers, such as human keratin fibers, with a lightening effect, comprising:

a) applying to the keratin fibers a composition disclosed herein for a time that is sufficient to develop the desired coloration and lightening, b) optionally rinsing the keratin fibers, c) optionally washing the keratin fibers with shampoo and rinsing the keratin fibers, and d) drying the keratin fibers or leaving the keratin fibers to dry.

Also disclosed herein is a process for coloring dark skin with a lightening effect, comprising applying to the skin a composition disclosed herein and drying the skin or leaving the skin to dry.

Everything that has been described previously regarding the various constituent components of the composition remains valid, and reference may be made thereto.

For example, the processes disclosed herein are suitable for treating human keratin fibers, such as artificially colored or pigmented hair, and dark skin.

In one embodiment, the keratin fibers that may be treated with the process as disclosed herein have a tone height of less than or equal to 6 (dark blond) such as less than or equal to 4 (chestnut-brown).

Furthermore, a dark skin capable of being treated in accordance with the disclosure has a lightness $L^*$, measured in the CIEL $L^*a^*b^*$ system, of less than or equal to 45 such as less than or equal to 40.

In a first embodiment, the process of dyeing keratin fibers with a lightening effect is performed with a composition that does not comprise any oxidation dyes or coupler and in the absence of oxidizing agent.

In a second embodiment, the process of dyeing keratin fibers with a lightening effect is performed with a composition that does not comprise any oxidation dyes or coupler, but in the presence of at least one oxidizing agent.

According to one embodiment of the dyeing processes disclosed herein, at least one composition as defined above is applied to the keratin fibers, such as the hair, for a time that is sufficient to develop the desired coloration and lightening, the keratin fibers are rinsed, optionally washed with shampoo, rinsed again and dried.

According to a second embodiment of the dyeing processes disclosed herein, at least one composition as defined above is applied to the keratin fibers, such as the hair, for a time that is sufficient to develop the desired coloration and lightening, without final rinsing.

According to a third embodiment of the dyeing process disclosed herein, the dyeing process comprises a preliminary operation that comprises separately storing, on the one hand, a composition disclosed herein optionally comprising, in addition to the at least one fluorescent dye and the at least one polyol, at least one oxidation base and/or one coupler, and, on the other hand, a composition comprising, in a cosmetically acceptable medium, at least one oxidizing agent, mixing them together at the time of use, applying the mixture to the keratin fibers, such as the hair, for a time that is sufficient to develop the desired coloration, rinsing the keratin fibers, optionally washing the keratin fibers with shampoo, rinsing the keratin fibers again and drying the keratin fibers.

The time required to develop the coloration and to obtain the lightening effect on the keratin fibers, such as the hair, can range, for example, from 5 to 60 minutes, such as from 5 to 40 minutes.

The temperature required to develop the coloration and to obtain the lightening effect may range, for example, from room temperature (15 to 25° C.) to 80° C., such as from 15 to 40° C.

Further disclosed herein is a multi-compartment device for dyeing keratin fibers, such as the hair, with a lightening effect, comprising at least one compartment comprising a composition disclosed herein, and at least one other compartment comprising a composition comprising at least one oxidizing agent. This device may be equipped with a means for applying the desired mixture to the keratin fibers, such as the devices described in French Patent No. 2 586 913.

It should be noted that the composition disclosed herein, if used to treat keratin fibers, such as chestnut-brown hair, makes it possible to achieve the following results:

If the reflectance of the hair is measured when it is irradiated with visible light in the wavelength range from 400 to 700 nanometers, and if the curves of reflectance as a function of the wavelength are compared for hair treated with the composition disclosed herein and untreated hair, it is found that the reflectance curve corresponding to the treated hair, in a wavelength range from 500 to 700 nanometers, is higher than that corresponding to the untreated hair.

This means that, in the wavelength range from 500 to 700 nanometers, such as from 540 to 700 nanometers, there is at least one range in which the reflectance curve corresponding to the treated hair is higher than the reflectance curve corresponding to the untreated hair. The term "higher than" means a difference of at least 0.05%, such as a difference of at least 0.1%, of reflectance.

However, there may be, within the wavelength range from 500 to 700 nanometers, such as from 540 to 700 nanometers, one or more ranges in which the reflectance curve corresponding to the treated fibers is either superimposable on or lower than the reflectance curve corresponding to the untreated fibers.

In one embodiment, the wavelength at which the difference is maximal between the reflectance curve for the treated hair and that for the untreated hair is in the wavelength range from 500 to 650 nanometers, such as in the wavelength range from 550 to 620 nanometers.

In addition, for example, the composition disclosed herein is capable of lightening the hair and the skin in a shade which, measured in the CIEL $L^*a^*b^*$ system, has a variable $b^*$ of greater than or equal to 6, with a $b^*$/absolute value of $a^*$ ratio of greater than 1.2 according to the selection test described below.

Selection Test

The composition is applied to chestnut-brown keratin fibers, such as the hair, at a rate of 10 grams of composition per 1 gram of chestnut-brown fibers. The composition is spread on so as to cover all of the fibers. The composition is left to act for 20 minutes at room temperature (20 to 25° C.). The fibers are then rinsed with water and then washed with a shampoo based on lauryl ether sulphate. They are then dried. The spectrocolorimetric characteristics of the fibers are then measured in order to determine the $L^*a^*b^*$ coordinates.

In the CIEL $L^*a^*b^*$ system, $a^*$ and $b^*$ indicate two color axes: $a^*$ indicates the green/red color axis ($+a^*$ is red, $-a^*$ is green) and $b^*$ indicates the blue/yellow color axis ($+b^*$ is yellow and $-b^*$ is blue); values close to zero for $a^*$ and $b^*$ correspond to grey shades.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The examples that follow are intended to illustrate the disclosure without, however, limiting its scope.

EXAMPLES

Fluorescent Compound 93 g of 2-picoline were reacted with 120 g of 1,6-dibromohexane in dimethylformamide at 110° C. for 5 hours.

The precipitated product was recovered and filtered off.

109 g of the product obtained above were dissolved in methanol and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C, 62.43%; H, 6.40%; Br, 23.07%; N, 8.09%.

The formula is as follows: $C_{36}H_{44}N_4 \cdot 2Br$.

| Composition | Weight % |
| --- | --- |
| Fluorescent compound | 1% |
| Hexylene glycol | 7% |
| Distilled water | qs 100% |

Composition

The percentages are expressed by weight of active material.

Coloration

The composition was applied to locks of natural chestnut-brown hair (tone height 4) with a leave-in time of 20 minutes.

The locks were then rinsed and dried under a hood for 30 minutes.

A marked lightening effect was observed on the locks.

What is claimed is:

1. A composition, comprising, in a cosmetically acceptable medium,
    at least one fluorescent dye that is soluble in the medium, and
    at least one polyol with a molecular weight of less than 500 g/mol and comprising more than three carbon atoms, of formula (I):

$$R1-\underset{OH}{\underset{|}{\overset{R2}{\overset{|}{C}}}}-(A)n-\underset{OH}{\underset{|}{\overset{R3}{\overset{|}{C}}}}-R4 \qquad (I)$$

wherein:
A is a divalent radical of a hydrocarbon-based chain chosen from linear and branched, saturated and unsaturated hydrocarbon-based chains, optionally interrupted with from 2 to 10 hetero atoms and comprising from 1 to 35 carbon atoms,
$R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and
n is 0 or 1;
wherein the at least one fluorescent dye is chosen from dyes of the following formulae (F1) and (F3):

(F1)

(F3)

wherein:
$R_1$ and $R_2$, which may be identical or different, are each chosen from:
    a hydrogen atom;
    linear and branched alkyl radicals comprising from 1 to 10 carbon atoms, optionally interrupted and/or substituted with at least one entity chosen from hetero atoms and groups comprising at least one hetero atom and/or optionally substituted with at least one halogen atom;

aryl and arylalkyl radicals, wherein the aryl group comprises 6 carbon atoms and the alkyl radical comprises from 1 to 4 carbon atoms; the aryl radical is optionally substituted with at least one alkyl radical chosen from linear and branched alkyl radicals comprising from 1 to 4 carbon atoms optionally interrupted and/or substituted with at least one entity chosen from hetero atoms and groups comprising at least one hetero atom and/or optionally substituted with at least one halogen atom;

$R_1$ and $R_2$ may optionally be linked so as to form a heterocycle with the nitrogen atom and may comprise at least one other hetero atom, wherein the heterocycle is optionally substituted with at least one alkyl radical chosen from linear and branched alkyl radicals and is optionally interrupted and/or substituted with at least one entity chosen from hetero atoms and groups comprising at least one hetero atom and/or optionally substituted with at least one halogen atom; and $R_1$ or $R_2$ may optionally be engaged in a heterocycle comprising the nitrogen atom and one of the carbon atoms of the phenyl group bearing said nitrogen atom;

$R_3$ and $R_4$, which may be identical or different, are each chosen from a hydrogen atom and alkyl radicals comprising from 1 to 4 carbon atoms;

$R_5$, which may be identical or different, are each chosen from a hydrogen atom, halogen atoms, and linear and branched alkyl radicals comprising from 1 to 4 carbon atoms, optionally interrupted with at least one hetero atom;

$R_6$, which may be identical or different, are each chosen from a hydrogen atom; halogen atoms; linear and branched alkyl radicals comprising from 1 to 4 carbon atoms, optionally substituted and/or interrupted with at least one entity chosen from hetero atoms and groups bearing at least one hetero atom and/or optionally substituted with at least one halogen atom;

X is chosen from:
  linear and branched alkyl radicals comprising from 1 to 14 carbon atoms and alkenyl radicals comprising from 2 to 14 carbon atoms, optionally interrupted and/or substituted with at least one entity chosen from hetero atoms and groups bearing at least one hetero atom and/or optionally substituted with at least one halogen atom;
  5- and 6-membered heterocyclic radicals optionally substituted with at least one alkyl radical chosen from linear and branched alkyl radicals comprising from 1 to 14 carbon atoms, optionally substituted with at least one hetero atom; optionally substituted with at least one aminoalkyl radical chosen from linear and branched aminoalkyl radicals comprising from 1 to 4 carbon atoms, optionally substituted with at least one hetero atom; and optionally substituted with at least one halogen atom;
  fused and non-fused, aromatic and diaromatic radicals, optionally separated with at least one alkyl radical chosen from alkyl radicals comprising from 1 to 4 carbon atoms, wherein at least one of the aryl radicals is optionally substituted with at least one halogen atom or with at least one alkyl radical chosen from alkyl radicals comprising from 1 to 10 carbon atoms optionally substituted and/or interrupted with at least one entity chosen from hetero atoms and groups bearing at least one hetero atom; and
  a dicarbonyl radical;
  provided that the group X possibly bears at least one cationic charge;

a is equal to 0 or 1;

$Y^-$, which may be identical or different, are each an anion chosen from organic and mineral anions; and n is an integer at least equal to 2 and at most equal to the number of cationic charges present in the fluorescent compound.

2. The composition according to claim 1, wherein the hydrocarbon-based chain of the divalent radical A does not comprise any hetero atoms.

3. The composition according to claim 1, wherein the radical A is chosen from linear and branched alkylene groups comprising from 1 to 8 carbon atoms.

4. The composition according to claim 1, wherein the at least one polyol of the formula (I) is chosen from 1,4-butanediol, 1,5-pentanediol, 1,6-hexanediol, neopentyl glycol, isoprene glycol, hexylene glycol, 2,3-dimethyl-1,5-pentanediol, 2-methyl-1,3-propanediol, 3-methyl-1,5-pentanediol, 3-methyl-1,3,5-pentanetriol and 1,2,4-butanetriol.

5. The composition according to claim 1, wherein the at least one polyol of the formula (I) is present in an amount ranging from 0.01% to 30% by weight, relative to the total weight of the composition.

6. The composition according to claim 5, wherein the at least one polyol of the formula (I) is present in an amount ranging from 0.1% to 20% by weight, relative to the total weight of the composition.

7. The composition according to claim 6, wherein the at least one polyol of the formula (I) is present in an amount ranging from 0.5% to 10% by weight, relative to the total weight of the composition.

8. The composition according to claim 1, wherein the optionally neutralized fluorescent dye is soluble in the cosmetically acceptable medium to at least 0.001 g/l at a temperature ranging from 15° C. and 25° C.

9. The composition according to claim 8, wherein the optionally neutralized fluorescent dye is soluble in the cosmetic medium to at least 0.5 g/l at a temperature ranging from 15° C. to 25° C.

10. The composition according to claim 9, wherein the optionally neutralized fluorescent dye is soluble in the cosmetic medium to at least 1 g/l at a temperature ranging from 15° C. to 25° C.

11. The composition according to claim 10, wherein the optionally neutralized fluorescent dye is soluble in the cosmetic medium to at least 5 g/l at a temperature ranging from 15° C. to 25° C.

12. The composition according to claim 1, wherein the at least one fluorescent dye is chosen from dyes in the orange range.

13. The composition according to claim 1, wherein the at least one fluorescent dye provides a reflectance maximum that is in the wavelength range from 500 to 650 nanometers.

14. The composition according to claim 13, wherein the at least one fluorescent dye provides a reflectance maximum that is in the wavelength range from 550 to 620 nanometers.

15. The composition according to claim 1, wherein in the formula (F3) defining $R_1$ and $R_2$, the linear and branched alkyl radicals are chosen from linear and branched alkyl radicals comprising from 1 to 4 carbon atoms.

16. The composition according to claim 1, wherein in the formula (F3) defining $R_1$ and $R_2$, the heterocycle is optionally substituted with at least one alkyl radical chosen from linear and branched alkyl radicals comprising from 1 to 4 carbon atoms.

17. The composition according to claim 1, wherein the at least one fluorescent dye is present in an amount ranging from 0.01% to 20% by weight, relative to the total weight of the composition.

18. The composition according to claim 17, wherein the at least one fluorescent dye is present in an amount ranging from 0.05% to 10% by weight, relative to the total weight of the composition.

19. The composition according to claim 18, wherein the at least one fluorescent dye is present in an amount ranging from 0.1% to 5% by weight, relative to the total weight of the composition.

20. The composition according to claim 1, further comprising at least one additional non-fluorescent direct dye chosen from direct dyes of nonionic, cationic and anionic nature.

21. The composition according to claim 20, wherein the at least one additional non-fluorescent direct dye is chosen from nitrobenzene dyes, azo dyes, anthraquinone dyes, naphthoquinone dyes, benzoquinone dyes, indigoid dyes, and triarylmethane-based dyes.

22. The composition according to claim 20, wherein the at least one additional direct dye is present in an amount ranging from 0.0005% to 12% by weight, relative to the total weight of the composition.

23. The composition according to claim 1, wherein the composition is in the form of a lightening dyeing shampoo.

24. The composition according to claim 1, further comprising at least one oxidation base chosen from para-phenylenediamines, bis(phenyl)alkylened iamines, para-aminophenols, ortho-aminophenols and heterocyclic bases, and the acid and base addition salts thereof.

25. The composition according to claim 24, wherein the at least one oxidation base is present in an amount ranging from 0.0005% to 12% by weight, relative to the total weight of the composition.

26. The composition according to claim 24, further comprising at least one coupler chosen from meta-phenylenediamines, meta-aminophenols, meta-diphenols and heterocyclic couplers, and the acid and base addition salts thereof.

27. The composition according to claim 26, wherein the at least one coupler is present in an amount ranging from 0.0001% to 10% by weight, relative to the total weight of the composition.

28. The composition according to claim 1, further comprising at least one oxidizing agent.

29. The composition according to claim 28, wherein the at least one oxidizing agent is chosen from hydrogen peroxide, urea peroxide, alkali metal bromates, persalts, and enzymes.

30. The composition according to claim 29, wherein the persalts are chosen from perborates and persulphates.

31. The composition according to claim 29, wherein the enzymes are chosen from peroxidases and two-electron and four-electron oxidoreductases.

32. A process for dyeing human keratin fibers with a lightening effect, comprising:
   a) applying to the keratin fibers a composition for a time that is sufficient to develop desired coloration and lightening, wherein the composition comprises, in a cosmetically acceptable medium,
      at least one fluorescent dye that is soluble in the medium, and
      at least one polyol with a molecular weight of less than 500 g/mol and comprising more than three carbon atoms, of formula (I) below:

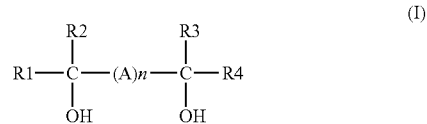

wherein:
A is divalent radical of a hydrocarbon-based chain chosen from linear and branched, saturated and unsaturated hydrocarbon-based chains, optionally interrupted with from 2 to 10 hetero atoms and comprising from 1 to 35 carbon atoms, $R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and n is 0 or 1;

wherein the at least one fluorescent dye is chosen from dyes of the following formulae (F1) and (F3):

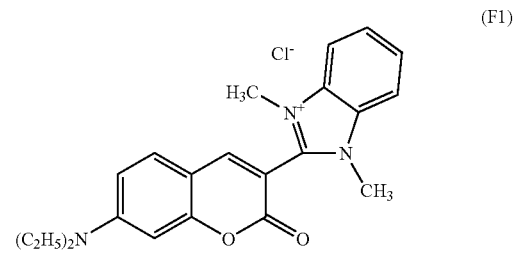

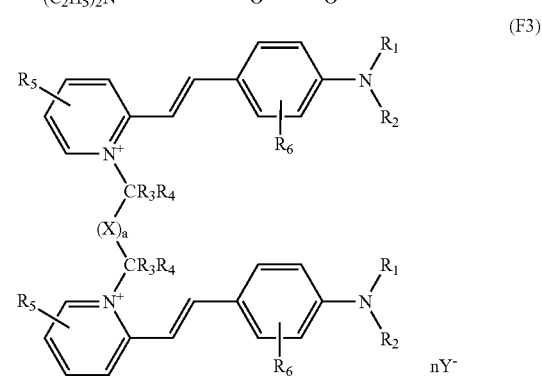

wherein:
$R_1$ and $R_2$, which may be identical or different, are each chosen from:

a hydrogen atom;

linear and branched alkyl radicals comprising from 1 to 10 carbon atoms, optionally interrupted and/or substituted with at least one entity chosen from hetero atoms and groups comprising at least one hetero atom and/or optionally substituted with at least one halogen atom;

aryl and arylalkyl radicals, wherein the aryl group comprises 6 carbon atoms and the alkyl radical comprises from 1 to 4 carbon atoms; the aryl radical is optionally substituted with at least one alkyl radical chosen from linear and branched alkyl radicals comprising from 1 to 4 carbon atoms optionally interrupted and/or substituted with at least one entity chosen from hetero atoms and groups comprising at least one hetero atom and/or optionally substituted with at least one halogen atom;

$R_1$ and $R_2$ may optionally be linked so as to form a heterocycle with the nitrogen atom and may comprise at least one other hetero atom, wherein the heterocycle is optionally substituted with at least one alkyl radical chosen from linear and branched alkyl radicals and is optionally interrupted and/or substituted with at least one entity chosen from hetero atoms and groups comprising at least one hetero atom and/or optionally substituted with at least one halogen atom; and $R_1$ or $R_2$ may optionally be engaged in a heterocycle comprising the nitrogen atom and one of the carbon atoms of the phenyl group bearing said nitrogen atom;

$R_3$ and $R_4$, which may be identical or different, are each chosen from a hydrogen atom and alkyl radicals comprising from 1 to 4 carbon atoms;

$R_5$, which may be identical or different, are each chosen from a hydrogen atom, halogen atoms, and linear and branched alkyl radicals comprising from 1 to 4 carbon atoms, optionally interrupted with at least one hetero atom;

$R_6$, which may be identical or different, are each chosen from a hydrogen atom; halogen atoms; linear and branched alkyl radicals comprising from 1 to 4 carbon atoms, optionally substituted and/or interrupted with at least one entity chosen from hetero atoms and groups bearing at least one hetero atom and/or optionally substituted with at least one halogen atom;

X is chosen from:
  linear and branched alkyl radicals comprising from 1 to 14 carbon atoms and alkenyl radicals comprising from 2 to 14 carbon atoms, optionally interrupted and/or substituted with at least one entity chosen from hetero atoms and groups bearing at least one hetero atom and/or optionally substituted with at least one halogen atom;
  5- and 6-membered heterocyclic radicals optionally substituted with at least one alkyl radical chosen from linear and branched alkyl radicals comprising from 1 to 14 carbon atoms, optionally substituted with at least one hetero atom; optionally substituted with at least one aminoalkyl radical chosen from linear and branched aminoalkyl radicals comprising from 1 to 4 carbon atoms, optionally substituted with at least one hetero atom; and optionally substituted with at least one halogen atom;
  fused and non-fused, aromatic and diaromatic radicals, optionally separated with at least one alkyl radical chosen from alkyl radicals comprising from 1 to 4 carbon atoms, wherein at least one of the aryl radicals is optionally substituted with at least one halogen atom or with at least one alkyl radical chosen from alkyl radicals comprising from 1 to 10 carbon atoms optionally substituted and/or interrupted with at least one entity chosen from hetero atoms and groups bearing at least one hetero atom; and
  a dicarbonyl radical;

provided that the group X possibly bears at least one cationic charge;

a is equal to 0 or 1;

$Y^-$, which may be identical or different, are each an anion chosen from organic and mineral anions; and n is an integer at least equal to 2 and at most equal to the number of cationic charges present in the fluorescent compound, b) optionally rinsing the keratin fibers, c) optionally washing the keratin fibers with shampoo and rinsing the keratin fibers, and d) drying the keratin fibers or leaving the keratin fibers to dry.

33. The process according to claim 32, further comprising a preliminary operation comprising separately storing, on the one hand, said composition, and, on the other hand, a composition comprising, in a cosmetically acceptable medium, at least one oxidizing agent, mixing together the two compositions at the time of use, applying this mixture to the keratin fibers for a time that is sufficient to develop the desired coloration, rinsing the keratin fibers, and optionally washing the keratin fibers with shampoo, rinsing the keratin fibers again and drying the keratin fibers.

34. The process according to claim 32, wherein the keratin fibers are hair with a tone height of less than or equal to 6.

35. The process according to claim 34, wherein the keratin fibers are hair with a tone height of less than or equal to 4.

36. A process for coloring dark skin with a lightening effect, comprising applying to the skin a composition comprising, in a cosmetically acceptable medium, at least one fluorescent dye that is soluble in the medium, and at least one polyol with a molecular weight of less than 500 g/mol and comprising more than three carbon atoms, of formula (I) below:

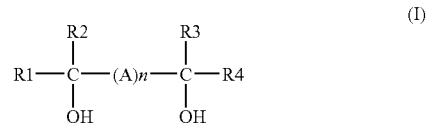

wherein:

A is divalent radical of a hydrocarbon-based chain chosen from linear and branched, saturated and unsaturated hydrocarbon-based chains, optionally interrupted with from 2 to 10 hetero atoms and comprising from 1 to 35 carbon atoms, $R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and n is 0 or 1;

and drying the skin or leaving the skin to dry, wherein the at least one fluorescent dye is chosen from dyes of the following formulae (F1) and (F3):

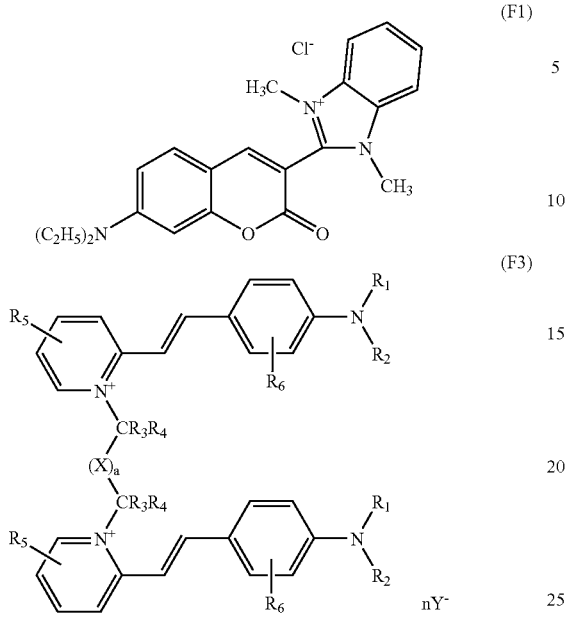

wherein:

R₁ and R₂ which may be identical or different, are each chosen from:
  a hydrogen atom;
  linear and branched alkyl radicals comprising from 1 to 10 carbon atoms, optionally interrupted and/or substituted with at least one entity chosen from hetero atoms and groups comprising at least one hetero atom and/or optionally substituted with at least one halogen atom;
  aryl and arylalkyl radicals, wherein the aryl group comprises 6 carbon atoms and the alkyl radical comprises from 1 to 4 carbon atoms; the aryl radical is optionally substituted with at least one alkyl radical chosen from linear and branched alkyl radicals comprising from 1 to 4 carbon atoms optionally interrupted and/or substituted with at least one entity chosen from hetero atoms and groups comprising at least one hetero atom and/or optionally substituted with at least one halogen atom;
  $R_1$ and $R_2$ may optionally be linked so as to form a heterocycle with the nitrogen atom and may comprise at least one other hetero atom, wherein the heterocycle is optionally substituted with at least one alkyl radical chosen from linear and branched alkyl radicals and is optionally interrupted and/or substituted with at least one entity chosen from hetero atoms and groups comprising at least one hetero atom and/or optionally substituted with at least one halogen atom; and
  $R_1$ or $R_2$ may optionally be engaged in a heterocycle comprising the nitrogen atom and one of the carbon atoms of the penyl group bearing said nitrogen atom;

$R_3$ and $R_4$, which may be identical or different, are each chosen from a hydrogen atom and alkyl radicals comprising from 1 to 4 carbon atoms;

$R_5$, which may be identical or different, are each chosen from a hydrogen atom, halogen atoms, and linear and branched alkyl radicals comprising from 1 to 4 carbon atoms, optionally interrupted with at least one hetero atom;

$R_6$, which may be identical or different, are each chosen from a hydrogen atom; halogen atoms; linear and branched alkyl radicals comprising from 1 to 4 carbon atoms, optionally substituted and/or interrupted with at least one entity chosen from hetero atoms and groups bearing at least one hetero atom and/or optionally substituted with at least one halogen atom;

X is chosen from:
  linear and branched alkyl radicals comprising from 1 to 14 carbon atoms and alkenyl radicals comprising from 2 to 14 carbon atoms, optionally interrupted and/or substituted with at least one entity chosen from hetero atoms and groups bearing at least one hetero atom and/or optionally substituted with at least one halogen atom;
  5- and 6-membered heterocyclic radicals optionally substituted with at least one alkyl radical chosen from linear and branched alkyl radicals comprising from 1 to 14 carbon atoms, optionally substituted with at least one hetero atom; optionally substituted with at least one aminoalkyl radical chosen from linear and branched aminoalkyl radicals comprising from 1 to 4 carbon atoms, optionally substituted with at least one hetero atom; and optionally substituted with at least one halogen atom;
  fused and non-fused, aromatic and diaromatic radicals, optionally separated with at least one alkyl radical chosen from alkyl radicals comprising from 1 to 4 carbon atoms, wherein at least one of the aryl radicals is optionally substituted with at least one halogen atom or with at least one alkyl radical chosen from alkyl radicals comprising from 1 to 10 carbon atoms optionally substituted and/or interrupted with at least one entity chosen from hetero atoms and groups bearing at least one hetero atom; and
  a dicarbonyl radical;
  provided that the group X possibly bears at least one cationic charge;

a is equal to 0 or 1;

$Y^-$, which may be identical or different, are each an anion chosen from organic and mineral anions; and n is an integer at least equal to 2 and at most equal to the number of cationic charges present in the fluorescent compound.

37. A multi-compartment device for dyeing and/or lightening human keratin fibers, comprising
  at least one compartment comprising a composition comprising, in a cosmetically acceptable medium,
    at least one fluorescent dye that is soluble in the medium, and
    at least one polyol with a molecular weight of less than 500 g/mol and comprising more than three carbon atoms, of formula (I) below:

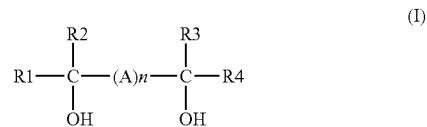

wherein:
A is divalent radical of a hydrocarbon-based chain chosen from linear and branched, saturated and unsaturated hydrocarbon-based chains, optionally interrupted with from 2 to 10 hetero atoms and comprising from 1 to 35 carbon atoms,
$R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and
n is 0 or 1;
wherein the at least one fluorescent dye is chosen from dyes of the following formulae (F1) and (F3):

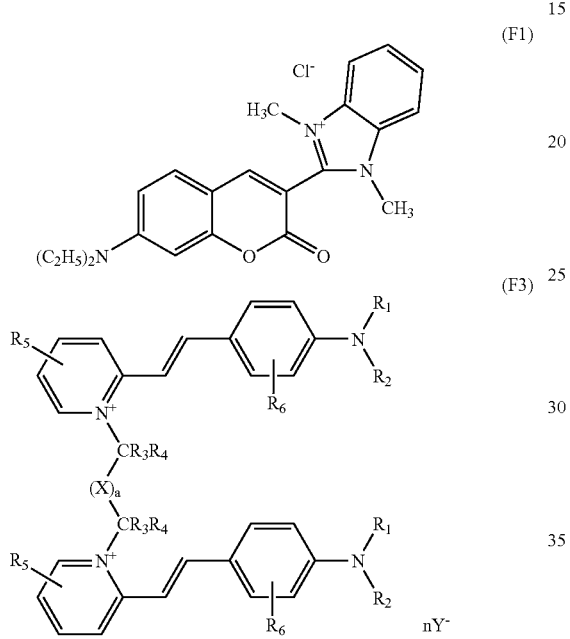

wherein:
$R_1$ and $R_2$, which may be identical or different, are each chosen from:
a hydrogen atom;
linear and branched alkyl radicals comprising from 1 to 10 carbon atoms, optionally interrupted and/or substituted with at least one entity chosen from hetero atoms and groups comprising at least one hetero atom and/or optionally substituted with at least one halogen atom;
aryl and arylalkyl radicals, wherein the aryl group comprises 6 carbon atoms and the alkyl radical comprises from 1 to 4 carbon atoms; the aryl radical is optionally substituted with at least one alkyl radical chosen from linear and branched alkyl radicals comprising from 1 to 4 carbon atoms optionally interrupted and/or substituted with at least one entity chosen from hetero atoms and groups comprising at least one hetero atom and/or optionally substituted with at least one halogen atom;
$R_1$ and $R_2$ may optionally be linked so as to form a heterocycle with the nitrogen atom and may comprise at least one other hetero atom, wherein the heterocycle is optionally substituted with at least one alkyl radical chosen from linear and branched alkyl radicals and is optionally interrupted and/or substituted with at least one entity chosen from hetero atoms and groups comprising at least one hetero atom and/or optionally substituted with at least one halogen atom; and
$R_1$ or $R_2$ may optionally be engaged in a heterocycle comprising the nitrogen atom and one of the carbon atoms of the phenyl group bearing said nitrogen atom;
$R_3$ and $R_4$, which may be identical or different, are each chosen from a hydrogen atom and alkyl radicals comprising from 1 to 4 carbon atoms;
$R_5$, which may be identical or different, are each chosen from a hydrogen atom, halogen atoms, and linear and branched alkyl radicals comprising from 1 to 4 carbon atoms, optionally interrupted with at least one hetero atom;
$R_6$, which may be identical or different, are each chosen from a hydrogen atom; halogen atoms; linear and branched alkyl radicals comprising from 1 to 4 carbon atoms, optionally substituted and/or interrupted with at least one entity chosen from hetero atoms and groups bearing at least one hetero atom and/or optionally substituted with at least one halogen atom;
X is chosen from;
linear and branched alkyl radicals comprising from 1 to 14 carbon atoms and alkenyl radicals comprising from 2 to 14 carbon atoms, optionally interrupted and/or substituted with at least one entity chosen from hetero atoms and groups bearing at least one hetero atom and/or optionally substituted with at least one halogen atom;
5- and 6-membered heterocyclic radicals optionally substituted with at least one alkyl radical chosen from linear and branched alkyl radicals comprising from 1 to 14 carbon atoms, optionally substituted with at least one hetero atom; optionally substituted with at least one aminoalkyl radical chosen from linear and branched aminoalkyl radicals comprising from 1 to 4 carbon atoms, optionally substituted with at least one hetero atom; and optionally substituted with at least one halogen atom;
fused and non-fused, aromatic and diaromatic radicals, optionally separated with at least one alkyl radical chosen from alkyl radicals comprising from 1 to 4 carbon atoms, wherein at least one of the aryl radicals is optionally substituted with at least one halogen atom or with at least one alkyl radical chosen from alkyl radicals comprising from 1 to 10 carbon atoms optionally substituted and/or interrupted with at least one entity chosen from hetero atoms and groups bearing at least one hetero atom; and
a dicarbonyl radical;
provided that the group X possibly bears at least one cationic charge;
a is equal to 0 or 1;
$Y^-$, which may be identical or different, are each an anion chosen from organic and mineral anions; and
n is an integer at least equal to 2 and at most equal to the number of cationic charges present in the fluorescent compound, and
at least one other compartment comprising a composition comprising at least one oxidizing agent.
38. A method for dyeing a human keratin material with a lightening effect, comprising applying to the keratin material a composition comprising, in a cosmetically acceptable medium,
at least one fluorescent dye that is soluble in the medium, and at least one polyol with a molecular weight of less than 500 g/mol and comprising more than three carbon atoms, of formula (I) below:

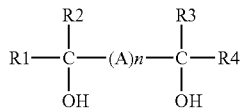

wherein:
A is divalent radical of a hydrocarbon-based chain chosen from linear and branched, saturated and unsaturated hydrocarbon-based chains, optionally interrupted with from 2 to 10 hetero atoms and comprising from 1 to 35 carbon atoms,
$R_1$, $R_2$, $R_3$ and $R_4$, which may be identical or different, are each chosen from a hydrogen atom, $C_1$–$C_2$ alkyl radicals and $C_1$–$C_6$ mono- and polyhydroxyalkyl radicals, and
n is 0 or 1;
wherein the at least one fluorescent dye is chosen from dyes of the following formulae (F1), (F3), and (F4):

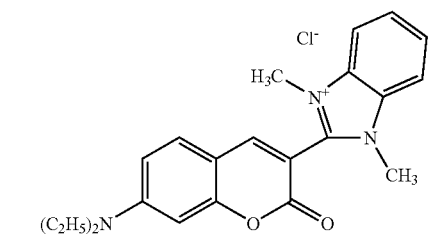

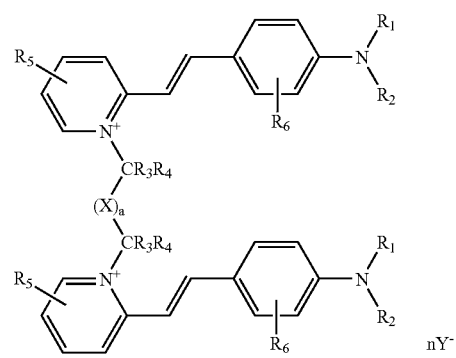

wherein:
$R_1$ and $R_2$, which may be identical or different, are each chosen from:
a hydrogen atom;
linear and branched alkyl radicals comprising from 1 to 10 carbon atoms, optionally interrupted and/or substituted with at least one entity chosen from hetero atoms and groups comprising at least one hetero atom and/or optionally substituted with at least one halogen atom;
aryl and arylalkyl radicals, wherein the aryl group comprises 6 carbon atoms and the alkyl radical comprises from 1 to 4 carbon atoms; the aryl radical is optionally substituted with at least one alkyl radical chosen from linear and branched alkyl radicals comprising from 1 to 4 carbon atoms optionally interrupted and/or substituted with at least one entity chosen from hetero atoms and groups comprising at least one hetero atom and/or optionally substituted with at least one halogen atom;
$R_1$ and $R_2$ may optionally be linked so as to form a heterocycle with the nitrogen atom and may comprise at least one other hetero atom, wherein the heterocycle is optionally substituted with at least one alkyl radical chosen from linear and branched alkyl radicals and is optionally interrupted and/or substituted with at least one entity chosen from hetero atoms and groups comprising at least one hetero atom and/or optionally substituted with at least one halogen atom; and
$R_1$, or $R_2$ may optionally be engaged in a heterocycle comprising the nitrogen atom and one of the carbon atoms of the phenyl group bearing said nitrogen atom;
$R_3$ and $R_4$, which may be identical or different, are each chosen from a hydrogen atom and alkyl radicals comprising from 1 to 4 carbon atoms;
$R_5$, which may be identical or different, are each chosen from a hydrogen atom, halogen atoms, and linear and branched alkyl radicals comprising from 1 to 4 carbon atoms, optionally interrupted with at least one hetero atom;
$R_6$, which may be identical or different, are each chosen from a hydrogen atom; halogen atoms; linear and branched alkyl radicals comprising from 1 to 4 carbon atoms, optionally substituted and/or interrupted with at least one entity chosen from hetero atoms and groups bearing at least one hetero atom and/or optionally substituted with at least one halogen atom;
X is chosen from:
linear and branched alkyl radicals comprising from 1 to 14 carbon atoms and alkenyl radicals comprising from 2 to 14 carbon atoms, optionally interrupted and/or substituted with at least one entity chosen from hetero atoms and groups bearing at least one hetero atom and/or optionally substituted with at least one halogen atom;
5- and 6-membered heterocyclic radicals optionally substituted with at least one alkyl radical chosen from linear and branched alkyl radicals comprising from 1 to 14 carbon atoms, optionally substituted with at least one hetero atom; optionally substituted with at least one aminoalkyl radical chosen from linear and branched aminoalkyl radicals comprising from 1 to 4 carbon atoms, optionally substituted with at least one hetero atom; and optionally substituted with at least one halogen atom;
fused and non-fused, aromatic and diaromatic radicals, optionally separated with at least one alkyl radical chosen from alkyl radicals comprising from 1 to 4 carbon atoms, wherein at least one of the aryl radicals is optionally substituted with at least one halogen atom or with at least one alkyl radical chosen from alkyl radicals comprising from 1 to 10 carbon atoms optionally substituted and/or interrupted with at least one entity chosen from hetero atoms and groups bearing at least one hetero atom; and
a dicarbonyl radical;
provided that the group X possibly bears at least one cationic charge;
a is equal to 0 or 1;
$Y^-$, which may be identical or different, are each an anion chosen from organic and mineral anions; and n is an integer at least equal to 2 and at most equal to the number of cationic charges present in the fluorescent compound; and

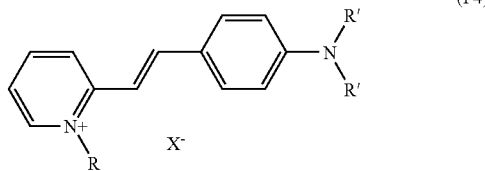

wherein R is chosen from methyl and ethyl radicals; R' is a methyl radical, and X⁻ is an anion.

39. The method according to claim 38, wherein the at least one fluorescent dye is chosen from dyes in the orange range.

40. The method according to claim 38, wherein the at least one fluorescent dye provides a reflectance maximum that is in the wavelength range from 500 to 650 nanometers.

41. The method according to claim 40, wherein the at least one fluorescent dye provides a reflectance maximum that is in the wavelength range from 550 to 620 nanometers.

42. The method according to claim 38, wherein in the formula (F3) defining $R_1$ and $R_2$, the linear and branched alkyl radicals are chosen from linear and branched alkyl radicals comprising from 1 to 4 carbon atoms.

43. The method according to claim 38, wherein in the formula (F3) defining $R_1$ and $R_2$, the heterocycle is optionally substituted with at least one alkyl radical chosen from linear and branched alkyl radicals comprising from 1 to 4 carbon atoms.

44. The method according to claim 38, wherein in the formula (F4), X⁻ is an anion chosen from chloride, iodide, sulphate, methasulphate, acetate, and perchlorate.

45. The method according to claim 38, wherein the at least one fluorescent dye is present in an amount ranging from 0.01% to 20% by weight, relative to the total weight of the composition.

46. The method according to claim 45, wherein the at least one fluorescent dye is present in an amount ranging from 0.05% to 10% by weight, relative to the total weight of the composition.

47. The method according to claim 46, wherein the at least one fluorescent dye is present in an amount ranging from 0.1% to 5% by weight, relative to the total weight of the composition.

48. The method according to claim 38, wherein the at least one polyol of the formula (I) is present in an amount ranging from 0.01% to 30% by weight, relative to the total weight of the composition.

49. The method according to claim 48, wherein the at least one polyol of the formula (I) is present in an amount ranging from 0.1% to 20% by weight, relative to the total weight of the composition.

50. The method according to claim 49, wherein the at least one polyol of the formula (I) is present in an amount ranging from 0.5% to 10% by weight, relative to the total weight of the composition.

51. The method according to claim 38, wherein the keratin material is chosen from artificially colored and pigmented keratin fibers and dark skin.

52. The method according to claim 51, wherein the keratin fibers are hair.

53. The method according to claim 52, wherein the hair has a tone height of less than or equal to 6.

54. The method according to claim 53, wherein the hair has a tone height of less than or equal to 4.

* * * * *

UNITED STATES PATENT AND TRADEMARK OFFICE
CERTIFICATE OF CORRECTION

| | |
|---|---|
| PATENT NO. | : 7,204,860 B2 |
| APPLICATION NO. | : 10/814300 |
| DATED | : April 17, 2007 |
| INVENTOR(S) | : Grégory Plos et al. |

It is certified that error appears in the above-identified patent and that said Letters Patent is hereby corrected as shown below:

Column 27, line 33, "bis(phenyl)alkylened iamines," should read --bis(phenyl)alkylenediamines,--.

Column 31, line 29, "$R_2$ which" should read --$R_2$, which--.

Column 31, line 62, "penyl" should read --phenyl--.

Column 36, line 15, "$R_1$, or" should read --$R_1$ or--.

Signed and Sealed this

Nineteenth Day of June, 2007

JON W. DUDAS
*Director of the United States Patent and Trademark Office*